United States Patent
Kasper et al.

(10) Patent No.: US 9,539,281 B2
(45) Date of Patent: Jan. 10, 2017

(54) LIPID-CONTAINING PSA COMPOSITIONS, METHODS OF ISOLATION AND METHODS OF USE THEREOF

(75) Inventors: Dennis L. Kasper, Brookline, MA (US); Deniz Erturk-Hasdemir, Worcester, MA (US); Barbara Reinap, Ashland, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/131,812

(22) PCT Filed: Jul. 12, 2012

(86) PCT No.: PCT/US2012/046384
§ 371 (c)(1),
(2), (4) Date: Apr. 7, 2014

(87) PCT Pub. No.: WO2013/009945
PCT Pub. Date: Jan. 17, 2013

(65) Prior Publication Data
US 2014/0243285 A1 Aug. 28, 2014

Related U.S. Application Data

(60) Provisional application No. 61/507,074, filed on Jul. 12, 2011.

(51) Int. Cl.
*C08B 37/00* (2006.01)
*A61K 31/739* (2006.01)
*C08L 5/00* (2006.01)
*A61K 35/74* (2015.01)

(52) U.S. Cl.
CPC ......... *A61K 31/739* (2013.01); *C08B 37/0003* (2013.01); *C08B 37/006* (2013.01); *C08L 5/00* (2013.01); *A61K 35/74* (2013.01)

(58) Field of Classification Search
None
See application file for complete search history.

(56) References Cited

U.S. PATENT DOCUMENTS

| | | | |
|---|---|---|---|
| 3,723,506 A | 3/1973 | Deslongchamps | |
| 3,849,550 A | 11/1974 | Teitelbaum et al. | |
| 4,316,982 A | 2/1982 | Holst | |
| 4,356,170 A | 10/1982 | Jennings et al. | |
| 4,619,995 A | 10/1986 | Hayes | |
| 4,740,480 A | 4/1988 | Ooka | |
| 4,775,626 A | 10/1988 | Armenta et al. | |
| 4,782,067 A | 11/1988 | Blythin et al. | |
| 4,819,617 A | 4/1989 | Goldberg | |
| 4,835,252 A | 5/1989 | Musso et al. | |
| 4,886,787 A | 12/1989 | de Belder et al. | |
| 4,937,270 A | 6/1990 | Hamilton et al. | |
| 4,952,524 A | 8/1990 | Lee et al. | |
| 5,126,141 A | 6/1992 | Henry | |
| 5,130,417 A | 7/1992 | Stanley et al. | |
| 5,140,016 A | 8/1992 | Goldberg et al. | |
| 5,158,939 A | 10/1992 | Takayama et al. | |
| 5,196,510 A | 3/1993 | Rodwell et al. | |
| 5,215,896 A | 6/1993 | Keck et al. | |
| 5,229,315 A | 7/1993 | Jun et al. | |
| 5,331,573 A | 7/1994 | Balaji et al. | |
| 5,468,676 A | 11/1995 | Madan | |
| 5,514,581 A | 5/1996 | Ferrari et al. | |
| 5,532,221 A | 7/1996 | Huang et al. | |
| 5,565,204 A | 10/1996 | Kuo et al. | |
| 5,576,002 A | 11/1996 | Jennings et al. | |
| 5,576,241 A | 11/1996 | Sakai | |
| 5,605,938 A | 2/1997 | Roufa et al. | |
| 5,679,654 A | 10/1997 | Tzianabos et al. | |
| 5,679,658 A | 10/1997 | Elson | |
| 5,700,787 A | 12/1997 | Tzianabos et al. | |
| 5,700,906 A | 12/1997 | Arnot et al. | |
| 5,705,178 A | 1/1998 | Roufa et al. | |
| 5,760,200 A | 6/1998 | Miller et al. | |
| 5,851,808 A | 12/1998 | Elledge et al. | |
| 5,853,718 A | 12/1998 | Molin et al. | |
| 5,868,870 A | 2/1999 | Fazan et al. | |
| 5,888,741 A | 3/1999 | Hendry | |
| 5,929,049 A | 7/1999 | Singh et al. | |
| 5,993,825 A | 11/1999 | Jennings et al. | |
| 6,027,733 A | 2/2000 | Wang et al. | |
| 6,110,672 A | 8/2000 | Mandel et al. | |
| 6,150,459 A | 11/2000 | Mayes et al. | |
| 6,274,144 B1 | 8/2001 | Wang et al. | |

(Continued)

FOREIGN PATENT DOCUMENTS

| CN | 1818061 A | 8/2006 |
|---|---|---|
| DE | 3704389 A1 | 8/1988 |

(Continued)

OTHER PUBLICATIONS

International Search Report and Written Opinion for PCT/US2012/046384 mailed Sep. 27, 2012.
International Preliminary Report on Patentability for PCT/US2012/046384 mailed Jan. 23, 2014.
Baumann et al., Structural elucidation of two capsular polysaccharides from one strain of Bacteroides fragilis using high-resolution NMR spectroscopy. Biochemistry. Apr. 28, 1992;31(16):4081-9.
Mazmanian et al., A microbial symbiosis factor prevents intestinal inflammatory disease. Nature. May 29, 2008;453(7195):620-5. doi: 10.1038/nature07008.
Ochoa-Repáraz et al., A polysaccharide from the human commensal Bacteroides fragilis protects against CNS demyelinating disease. Mucosal Immunol. Sep. 2010;3(5):487-95. doi: 10.1038/mi.2010.29. Epub Jun. 9, 2010.

(Continued)

*Primary Examiner* — Leigh C Maier
(74) *Attorney, Agent, or Firm* — Wolf, Greenfield & Sack, P.C.

(57) ABSTRACT

The invention provides compositions comprising lipid-conjugated forms of capsular polysaccharide A (PSA) from *B. fragilis* (referred to herein as PSA-LT), methods of isolating such forms and of making such compositions and methods for their use.

16 Claims, 12 Drawing Sheets

(56) References Cited

U.S. PATENT DOCUMENTS

| | | |
|---|---|---|
| 6,294,518 B1 | 9/2001 | Potter et al. |
| 6,358,939 B1 | 3/2002 | Hayes et al. |
| 6,447,765 B1 | 9/2002 | Horwitz |
| 6,670,146 B2 | 12/2003 | Barrat et al. |
| 6,995,237 B1 | 2/2006 | Zimmerman |
| 7,026,285 B2 | 4/2006 | Tzianabos et al. |
| 7,083,777 B1 | 8/2006 | Tzianabos et al. |
| 7,163,683 B2 | 1/2007 | Barstad et al. |
| 7,166,455 B2 | 1/2007 | Comstock et al. |
| 7,384,645 B2 | 6/2008 | Foster et al. |
| 7,629,330 B2 | 12/2009 | Wang et al. |
| 7,678,558 B2 | 3/2010 | Comstock et al. |
| 7,803,602 B2 | 9/2010 | Comstock et al. |
| 7,807,154 B2 | 10/2010 | Strasburger et al. |
| 8,008,276 B2 | 8/2011 | Wang et al. |
| 8,206,726 B2 | 6/2012 | Kasper et al. |
| 8,580,278 B2 | 11/2013 | Kasper et al. |
| 8,586,029 B2 | 11/2013 | Kasper et al. |
| 9,057,070 B2 | 6/2015 | Mazmanian et al. |
| 9,265,790 B2 | 2/2016 | Tzianabos et al. |
| 2001/0001788 A1 | 5/2001 | Satoh et al. |
| 2002/0022019 A1 | 2/2002 | Laulund |
| 2002/0090357 A1 | 7/2002 | Barrat et al. |
| 2002/0155436 A1 | 10/2002 | Classen |
| 2003/0044425 A1 | 3/2003 | Burt et al. |
| 2003/0059462 A1 | 3/2003 | Barenholz et al. |
| 2003/0147865 A1 | 8/2003 | Salomon et al. |
| 2003/0219413 A1 | 11/2003 | Comstock et al. |
| 2004/0039056 A1 | 2/2004 | Bollag et al. |
| 2004/0092433 A1 | 5/2004 | Wang et al. |
| 2004/0219160 A1 | 11/2004 | Tzianabos et al. |
| 2005/0020515 A1 | 1/2005 | Graff et al. |
| 2005/0063979 A1 | 3/2005 | Pickl et al. |
| 2005/0101012 A1 | 5/2005 | Schuler et al. |
| 2005/0119164 A1 | 6/2005 | Taylor et al. |
| 2005/0147624 A1 | 7/2005 | Jennings et al. |
| 2005/0181021 A1 | 8/2005 | Lamb |
| 2005/0271643 A1 | 12/2005 | Sorokulova et al. |
| 2006/0014717 A1 | 1/2006 | Angstrom et al. |
| 2006/0110412 A1 | 5/2006 | Desmons et al. |
| 2006/0116332 A1 | 6/2006 | Strober et al. |
| 2006/0153832 A1 | 7/2006 | Tzianabos et al. |
| 2006/0257852 A1 | 11/2006 | Rappuoli et al. |
| 2006/0275752 A1 | 12/2006 | Sindhi |
| 2007/0020730 A1 | 1/2007 | Comstock et al. |
| 2007/0154991 A1 | 7/2007 | Comstock et al. |
| 2007/0207526 A1 | 9/2007 | Coit et al. |
| 2007/0238747 A1 | 10/2007 | van Duzer et al. |
| 2008/0057565 A1 | 3/2008 | Comstock et al. |
| 2008/0131445 A1 | 6/2008 | Bluestone et al. |
| 2008/0286252 A1 | 11/2008 | Sinnott |
| 2009/0017472 A1 | 1/2009 | Stuhlmuller et al. |
| 2009/0124573 A1 | 5/2009 | Mazmanian et al. |
| 2009/0252708 A1 | 10/2009 | Fitzpatrick et al. |
| 2009/0317410 A1 | 12/2009 | Wang et al. |
| 2009/0317427 A1 | 12/2009 | Kasper et al. |
| 2010/0080760 A1 | 4/2010 | Hyde et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330166 A1 | 12/2010 | Ishida et al. |
| 2011/0002965 A1 | 1/2011 | Round et al. |
| 2011/0009360 A1 | 1/2011 | Kasper et al. |
| 2011/0059125 A1 | 3/2011 | Tzianabos et al. |
| 2011/0086011 A1 | 4/2011 | Kasper et al. |
| 2011/0150852 A1 | 6/2011 | Chambaud et al. |
| 2011/0251156 A1* | 10/2011 | Shen et al. ............... 514/54 |
| 2011/0287048 A1 | 11/2011 | Round et al. |
| 2012/0087895 A1 | 4/2012 | Mazmanian et al. |
| 2012/0094950 A1 | 4/2012 | Kasper et al. |
| 2012/0309955 A1 | 12/2012 | Kasper et al. |
| 2012/0315264 A1 | 12/2012 | Tzianabos et al. |
| 2013/0039949 A1 | 2/2013 | Mazmanian et al. |
| 2013/0064859 A1 | 3/2013 | Mazmanian et al. |
| 2013/0121966 A1 | 5/2013 | Mazmanian et al. |
| 2013/0195802 A1 | 8/2013 | Moore |
| 2014/0030807 A1 | 1/2014 | Kasper et al. |
| 2014/0072534 A1 | 3/2014 | Mazmanian et al. |
| 2014/0099331 A1 | 4/2014 | Tzianabos et al. |
| 2014/0243285 A1 | 8/2014 | Kasper et al. |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |

FOREIGN PATENT DOCUMENTS

| | | |
|---|---|---|
| EP | 0382576 A1 | 8/1990 |
| EP | 0497524 A2 | 8/1992 |
| EP | 1358885 A1 | 11/2003 |
| EP | 1459757 A1 | 9/2004 |
| EP | 0371414 A2 | 6/2006 |
| GB | 2286193 A | 8/1995 |
| JP | 56128721 | 10/1981 |
| JP | H10-507746 | 7/1998 |
| JP | 2002541113 | 12/2002 |
| JP | 2004536028 | 12/2004 |
| JP | 2006522135 | 9/2006 |
| JP | 2012-524910 A | 10/2012 |
| WO | WO 95/31990 A1 | 11/1995 |
| WO | WO 96/07427 A1 | 3/1996 |
| WO | WO 96/32119 A1 | 10/1996 |
| WO | WO 96/35433 A1 | 11/1996 |
| WO | WO 98/42718 A1 | 10/1998 |
| WO | WO 98/45335 A1 | 10/1998 |
| WO | WO 00/01733 A1 | 1/2000 |
| WO | WO 00/59515 A2 | 10/2000 |
| WO | WO 02/07741 A1 | 1/2002 |
| WO | WO 02/45708 A2 | 6/2002 |
| WO | WO 03/075953 A2 | 9/2003 |
| WO | WO 03/077863 A2 | 9/2003 |
| WO | WO 03/095606 A2 | 11/2003 |
| WO | WO 2004/050909 A2 | 6/2004 |
| WO | WO 2004/089407 A2 | 10/2004 |
| WO | WO 2005/010215 A2 | 2/2005 |
| WO | WO 2007/040446 A1 | 4/2007 |
| WO | WO 2007/092451 A2 | 8/2007 |
| WO | WO 2008/095141 A2 | 8/2008 |
| WO | WO 2009/062132 A2 | 5/2009 |
| WO | WO 2009/149149 A1 | 12/2009 |
| WO | WO 2010/124256 A2 | 10/2010 |
| WO | WO 2011/056703 A1 | 5/2011 |
| WO | WO 2011/127302 A2 | 10/2011 |
| WO | WO 2011/146910 A1 | 11/2011 |
| WO | WO 2011/153226 A2 | 12/2011 |
| WO | WO 2012/027032 A1 | 3/2012 |
| WO | WO 2012/103532 A1 | 8/2012 |
| WO | WO 2013/009945 A1 | 1/2013 |
| WO | WO 2013/019896 A1 | 2/2013 |
| WO | WO 2013/036290 A1 | 3/2013 |
| WO | WO 2013/052099 A2 | 4/2013 |
| WO | WO 2014/182966 A1 | 11/2014 |

OTHER PUBLICATIONS

Pantosti et al., Immunochemical characterization of two surface polysaccharides of Bacteroides fragilis. Infect Immun. Jun. 1991;59(6):2075-82.

Ruiz-Perez et al., Modulation of surgical fibrosis by microbial zwitterionic polysaccharides. Proc Natl Acad Sci U S A. Nov. 15, 2005;102(46):16753-8. Epub Nov. 7, 2005.

Tzianabos et al., The capsular polysaccharide of Bacteroides fragilis comprises two ionically linked polysaccharides. J Biol Chem. Sep. 5, 1992;267(25):18230-5.

Tzianabos et al., T cells activated by zwitterionic molecules prevent abscesses induced by pathogenic bacteria. J Biol Chem. Mar. 10, 2000;275(10):6733-40.

Tzianabos et al., Structural features of polysaccharides that induce intra-abdominal abscesses. Science. Oct. 15, 1993;262(5132):416-9.

Extended European Search Report for Application No. 12811896.5, mailed Jun. 1, 2015.

(56) References Cited

OTHER PUBLICATIONS

GenBank Accession No. AJ277832; Hutloff Jan. 19, 2001.
GenBank Accession No. CAC06612; Hutloff Jan. 19, 2001.
GenBank Accession No. NM.sub.—012092; Dec. 20, 2003.
GenBank Accession No. NP.sub.—036224 Dec. 20, 2003.
No Author Listed, Excerpts from Immunobiology, 7th ed. 2008. Part IV: The Adaptive Immune Response. Chapter 9 T Cell-Mediated Immunity.
No Author Listed, Acute Respiratory Disease Syndrome: What is acute respiratory disease syndrome? American Lung Association. 3 pages. http://www.lungusa.org/site/apps/nlnet/content3.aspx?c=dvLUK9O0E&b=2058817&content. Sep. 24, 2008.
No Author Listed, Lupus study. Meet a Lupus Researcher. www.lupusstudy.org/updates.php. Nov. 2005; 1-2.
No Author Listed, Polyethylene Glycols (PEGs). Accessed Mar. 7, 2005. 1 page. http://www.mindfully.org/Plastic/Polymers/Polyethylene-Glycols-PEGs.htm.
No Author Listed, The Merck Index. Eleventh Edition 1989:734-735.
No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.
Abreu et al., Measurement of vitamin D levels in inflammatory bowel disease patients reveals a subset of Crohn's disease patients with elevated 1,25-dihydroxyvitamin D and low bone mineral density. Gut. Aug. 2004;53(8):1129-36.
Adams et al., Extrarenal expression of the 25-hydroxyvitamin D-1-hydroxylase. Arch Biochem Biophys. Jul. 1, 2012;523(1):95-102. doi: 10.1016/j.abb.2012.02.016. Epub Mar. 14, 2012.
Adams et al., Unexpected actions of vitamin D: new perspectives on the regulation of innate and adaptive immunity. Nat Clin Pract Endocrinol Metab. Feb. 2008;4(2):80-90. doi: 10.1038/ncpendmet0716.
Adkins et al., Early block in maturation is associated with thymic involution in mammary tumor-bearing mice. J Immunol. Jun. 1, 2000;164(11):5635-40.
Adkins et al., Exclusive Th2 primary effector function in spleens but mixed Th1/Th2 function in lymph nodes of murine neonates. J Immunol. Mar. 1, 2000;164(5):2347-53.
Afzali, The role of T helper 17 (Th17) and regulatory T cells (Treg) in human organ transplantation and autoimmune disease. Clin Exp Immunol. Apr. 2007;148(1):32-46.
Aharoni et al., Copolymer 1 induces T cells of the T helper type 2 that crossreact with myelin basic protein and suppress experimental autoimmune encephalomyelitis. Proc Natl Acad Sci U S A. Sep. 30, 1997;94(20):10821-6.
Aharoni et al., Bystander suppression of experimental autoimmune encephalomyelitis by T cell lines and clones of the Th2 type induced by copolymer 1. J Neuroimmunol. Nov. 2, 1998;91(1-2);135-46.
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Al-Bader et al., Activation of human dendritic cells is modulated by components of the outer membranes of Neisseria meningitidis. Infect Immun. Oct. 2003;71(10):5590-7.
Allen et al., A pilot study of the immunological effects of high-dose vitamin D in healthy volunteers. Mult Scler. Dec. 2012;18(12):1797-800. doi: 10.1177/1352458512442992. Epub Mar. 28, 2012.
Amsen et al., Instruction of distinct CD4 T helper cell fates by different notch ligands on antigen-presenting cells. Cell. May 14, 2004;117(4):515-26.
Anderson et al., A transgenic model of central nervous system autoimmunity mediated by CD4+ and CD8+ T and B cells. J Immunol. Mar. 1, 2012;188(5):2084-92. doi: 10.4049/jimmunol.1102186. Epub Jan. 25, 2012.
Arnon et al., New insights into the mechanism of action of copolymer 1 in experimental allergic encephalomyelitis and multiple sclerosis. J Neurol. Apr. 1996;243(4 Suppl 1):S8-13. Review.

Asadullah et al., Interleukin-10 therapy—review of a new approach. Pharmacol Rev. Jun. 2003;55(2):241-69.
Ascherio et al., Vitamin D and multiple sclerosis. Lancet Neurol. Jun. 2010;9(6):599-612. doi: 10.1016/S1474-4422(10)70086-7.
Asseman et al., An essential role for interleukin 10 in the function of regulatory T cells that inhibit intestinal inflammation. J Exp Med. Oct. 4, 1999;190(7):995-1004.
Atarashi et al., ATP drives lamina propria T(H)17 cell differentiation. Nature. Oct. 9, 2008;455(7214):808-12. doi: 10.1038/nature07240. Epub Aug. 20, 2008.
Awasthi et al., Interplay between effector Th17 and regulatory T cells. J Clin Immunol. Nov. 2008;28(6):660-70. doi: 10.1007/s10875-008-9239-7. Epub Sep. 23, 2008.
Azzawi et al., Identification of activated T lymphocytes and eosinophils in bronchial biopsies in stable atopic asthma. Am Rev Respir Dis. Dec. 1990;142(6 Pt 1):1407-13.
Bach, The effect of infections on susceptibility to autoimmune and allergic diseases. N Engl J Med. Sep. 19, 2002;347(12):911-20.
Baecher-Allan et al., CD2 costimulation reveals defective activity by human CD4+CD25(hi) regulatory cells in patients with multiple sclerosis. J Immunol. Mar. 15, 2011;186(6):3317-26. doi: 10.4049/jimmunol.1002502. Epub Feb. 7, 2011.
Banerjee et al., Expansion of FOXP3high regulatory T cells by human dendritic cells (DCs) in vitro and after injection of cytokine-matured DCs in myeloma patients. Blood. Oct. 15, 2006;108(8):2655-61. Epub Jun. 8, 2006.
Bar-On et al., Defining in vivo dendritic cell functions using CD11c-DTR transgenic mice. Methods Mol Biol. 2010;595:429-42. doi: 10.1007/978-1-60761-421-0_28.
Baranzini et al., Genome, epigenome and RNA sequences of monozygotic twins discordant for multiple sclerosis. Nature. Apr. 29, 2010;464(7293):1351-6. doi: 10.1038/nature08990.
Barnes et al., Regulatory T cells reinforce intestinal homeostasis. Immunity. Sep. 18, 2009;31(3):401-11. doi: 10.1016/j.immuni.2009.08.011.
Barrat et al., In vitro generation of interleukin 10-producing regulatory CD4(+) T cells is induced by immunosuppressive drugs and inhibited by T helper type 1 (Th1)- and Th2-inducing cytokines. J Exp Med. Mar. 4, 2002;195(5):603-16.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.
Batta et al., Conformational stabilization of the altruronic acid residue in the O-specific polysaccharide of Shigella sonnei/Plesiomonas shigelloides. Carbohydr Res. Dec. 1997;305(1):93-9.
Bayley DP et al. Analysis of cepA and other Bacteroides fragilis genes reveals a unique promoter structure. (2000) FEMS Microbiol Lett 193:149-54.
Bazan et al., Unraveling the structure of IL-2. Science. Jul. 17, 1992;257(5068):410-3.
Becker et al., Clustering of non-major histocompatibility complex susceptibility candidate loci in human autoimmune diseases. Proc Natl Acad Sci U S A. Aug. 18, 1998;95(17):9979-84.
Belkaid et al., Regulatory T cells in the control of host-microorganism interactions (*). Annu Rev Immunol. 2009;27:551-89. doi: 10.1146/annurev.immunol.021908.132723.
Berer et al., Commensal gut flora and brain autoimmunity: a love or hate affair? Acta Neuropathol. May 2012;123(5):639-51. doi: 10.1007/s00401-012-0949-9. Epub Feb. 10, 2012.
Berer et al., Commensal microbiota and myelin autoantigen cooperate to trigger autoimmune demyelination. Nature. Oct. 26, 2011;479(7374):538-41. doi: 10.1038/nature10554.
Berggren et al., Decreasing serum concentrations of all-trans, 13-cis retinoic acids and retinol during fasting and caloric restriction. J Intern Med. Mar. 2003;253(3):375-80.
Bernatowska-Matuskiewicz et al., IgG subclasses and antibody response to pneumococcal capsular polysaccharides in children with severe sinopulmonary infections and sathma. Immunol Invest. 1991;20(2):173-185.

(56) References Cited

OTHER PUBLICATIONS

Bettelli et al., Myelin oligodendrocyte glycoprotein-specific T cell receptor transgenic mice develop spontaneous autoimmune optic neuritis. J Exp Med. May 5, 2003;197(9):1073-81.
Bettelli et al., Reciprocal developmental pathways for the generation of pathogenic effector TH17 and regulatory T cells. Nature. May 11, 2006;441(7090):235-8. Epub Apr. 30, 2006.
Bhat et al., Innate and adaptive autoimmunity directed to the central nervous system. Neuron. Oct. 15, 2009;64(1):123-32. doi: 10.1016/j.neuron.2009.09.015.
Bilo, B.M., et al., Diagnosis of Hymenoptera venom allergy; Allergy 2005; 60:1339-1349.
Blomfield et al. Lrp stimulates phase variation of type 1 fimbriation in E. coli K12. J. Bacteriology 175, 27-36, 1993.
Boes et al., Accelerated development of IgG autoantibodies and autoimmune disease in the absence of secreted IgM. Proc Natl Acad Sci U S A. Feb. 1, 2000;97(3):1184-9.
Boguniewicz, M.; The autoimmune nature of chronic urticaria; Allergy Asthma Proc 2008; 29:433-438.
Borsellino et al., Expression of ectonucleotidase CD39 by Foxp3+ Treg cells: hydrolysis of extracellular ATP and immune suppression. Blood. Aug. 15, 2007; 110(4):1225-32. Epub Apr. 20, 2007.
Bouma et al., The immunological and genetic basis of inflammatory bowel disease. Nat Rev Immunol. Jul. 2003;3(7):521-33.
Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.
Braun et al., Body traffic: ecology, genetics, and immunity in inflammatory bowel disease. Annu Rev Pathol. 2007;2:401-29.
Brubaker et al., Mitogenic activity of purified capsular polysaccharide A from Bacteroides fragilis: differential stimulatory effect on mouse and rat lymphocytes in vitro. J Immunol. Feb. 15, 1999;162(4):2235-42.
Bruce et al., Converging pathways lead to overproduction of IL-17 in the absence of vitamin D signaling. Int Immunol. Aug. 2011;23(8):519-28. doi: 10.1093/intimm/dxr045. Epub Jun. 22, 2011.
Brunkow et al., Disruption of a new forkhead/winged-helix protein, scurfin, results in the fatal lymphoproliferative disorder of the scurfy mouse. Nat Genet. Jan. 2001;27(1):68-73.
Budinger et al., Immunologic mechanisms in hypersensitivity reactions to metal ions: an overview. Allergy. Feb. 2000;55(2):108-15. Review.
Burgers et al., The challenges of HIV vaccine development and testing. Best Pract Res Clin Obstet Gynaecol. Apr. 2005;19(2):277-91.
Cabrera et al., Influence of serum and soluble CD25 (sCD25) on regulatory and effector T-cell function in hepatocellular carcinoma. Scand J Immunol. Oct. 2010;72(4):293-301. doi: 10.1111/j.1365-3083.2010.02427.x.
Cahill et al., Inflammatory bowel disease: an immunity-mediated condition triggered by bacterial infection with Helicobacter hepaticus. Infect Immun. Aug. 1997;65(8):3126-31.
Campbell et al., The vitamin D receptor as a therapeutic target. Expert Opin Ther Targets. Oct. 2006;10(5):735-48.
Cantorna et al., 1,25-Dihydroxycholecalciferol prevents and ameliorates symptoms of experimental murine inflammatory bowel disease. J Nutr. Nov. 2000;130(11):2648-52.
Cantorna et al., Vitamin D status, 1,25-dihydroxyvitamin D3, and the immune system. Am J Clin Nutr. Dec. 2004;80(6 Suppl):1717S-20S.
Cantorna et al., 1,25-Dihydroxyvitamin D3 reversibly blocks the progression of relapsing encephalomyelitis, a model of multiple sclerosis. Proc Natl Acad Sci U S A. Jul. 23, 1996;93(15):7861-4.
Cash et al., Symbiotic bacteria direct expression of an intestinal bactericidal lectin. Science. Aug. 25, 2006;313(5790):1126-30.
Chambers et al., The impact of vitamin D on regulatory T cells. Curr Allergy Asthma Rep. Feb. 2011;11(1):29-36. doi: 10.1007/s11882-010-0161-8.
Chang et al., 1,25-Dihydroxyvitamin D3 inhibits the differentiation and migration of T(H)17 cells to protect against experimental autoimmune encephalomyelitis. PLoS One. Sep. 23, 2010;5(9):e12925. doi: 10.1371/journal.pone.0012925.
Chatila et al., Role of regulatory T cells in human diseases. J Allergy Clin Immunol. Nov. 2005;116(5):949-59; quiz 960.
Chen et al., Pertussis toxin by inducing IL-6 promotes the generation of IL-17-producing CD4 cells. J Immunol. May 15, 2007;178(10):6123-9.
Chen et al., Delivery of foreign antigens by engineered outer membrane vesicle vaccines. Proc Natl Acad Sci U S A. Feb. 16, 2010;107(7):3099-104. doi: 10.1073/pnas.0805532107. Epub Jan. 27, 2010.
Chen J et al., DNA inversion on conjugative plasmid pVT745. J Bacteriol. Nov. 2002;184(21):5926-34.
Cho et al., Recent insights into the genetics of inflammatory bowel disease. Gastroenterology. May 2011;140(6):1704-12. doi: 10.1053/j.gastro.2011.02.046.
Chow et al., Getting the bugs out of the immune system: do bacterial microbiota "fix" intestinal T cell responses? Cell Host Microbe. Jan. 22, 2009;5(1):8-12. doi: 10.1016/j.chom.2008.12.006.
Cobb et al., Zwitterionic capsular polysaccharides: the new MHCII-dependent antigens. Cell Microbiol. Oct. 2005;7(10):1398-403. Review.
Collison et al., The inhibitory cytokine IL-35 contributes to regulatory T-cell function. Nature. Nov. 22, 2007;450(7169):566-9.
Comstock et al., Bacterial glycans: key mediators of diverse host immune responses. Cell. Sep. 8, 2006;126(5):847-50.
Comstock et al., Interstrain variation of the polysaccharide B biosynthesis locus of Bacteroides fragilis: characterization of the region from strain 638R. J Bacteriol. Oct. 1999;181(19):6192-6.
Comstock Le et al. Analysis of a capsular polysaccharide biosynthesis locus of Bacteroides fragilis. (1999) Infect Immun 67:3525-32.
Conesa et al., Interleukin-2 induces peroxide production by primed normodense eosinophils of patients with asthma. Allergy Asthma Proc. Jan.-Feb. 2003;24(1):27-33.
Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.
Coombes et al., Control of intestinal homeostasis by regulatory T cells and dendritic cells. Semin Immunol. Apr. 2007;19(2):116-26. Epub Feb. 21, 2007.
Coombes et al., Regulatory T cells and intestinal homeostasis. Immunol Rev. Apr. 2005;204:184-94.
Correale et al., Vitamin D-mediated immune regulation in multiple sclerosis. J Neurol Sci. Dec. 15, 2011;311(1-2):23-31. doi: 10.1016/j.jns.2011.06.027. Epub Jul. 2, 2011.
Couper et al., IL-10: the master regulator of immunity to infection. J Immunol. May 1, 2008;180(9):5771-7.
Coyne et al., Bacteroides fragilis NCTC9343 produces at least three distinct capsular polysaccharides: cloning, characterization, and reassignment of polysaccharide B and C biosynthesis loci. Infect Immun. Nov. 2000;68(11):6176-81.
Coyne M et al. Polysaccharide biosynthesis locus required for virulence of Bacteroides fragilis. (2001) Infect Immun 69:4342-50.
Coyne MJ et al., Mpi recombinase globally modulates the surface archtiecture of a human commensal bacterium. Proc Natl Acad Sci U S A. Sep. 2, 2003;100(18):10446-51. Epub Aug. 12, 2003.
Crabb et al., T cell regulation of Bacteroides fragilis-induced intraabdominal abscesses. Rev. Infect Dis. Jan.-Feb. 1990;12 Suppl 2:S178-84. Review.
Craig, Autologous hematopoietic stem cell transplantation for Crohn's disease. Autoimmun Rev. Aug. 2002;1(4):244-9. Review.
Dahiyat BI. et al., De novo protein design: fully automated sequence selection . Science (1997) 278:82-87.
Daniel et al., Immune modulatory treatment of trinitrobenzene sulfonic acid colitis with calcitriol is associated with a change of a T helper (Th) 1/Th17 to a Th2 and regulatory T cell profile. J Pharmacol Exp Ther. Jan. 2008;324(1):23-33. Epub Oct. 2, 2007.

(56) References Cited

OTHER PUBLICATIONS

Denning et al., Lamina propria macrophages and dendritic cells differentially induce regulatory and interleukin 17-producing T cell responses. Nat Immunol. Oct. 2007;8(10):1086-94. Epub Sep. 16, 2007.
Dethlefsen et al., An ecological and evolutionary perspective on human-microbe mutualism and disease. Nature. Oct. 18, 2007;449(7164):811-8.
Dias et al., Antisense oligonucleotides: Basic concepts and mechanisms. Mol. Cancer Therap., 2002, vol. 1: 347-355.
DiFabio et al., Structure of the Capsular Polysaccharide Antigen of Type IV Group B Streptococcus; Can. J. Chem. 67:877 (1989).
Dong, Diversification of T-helper-cell lineages: finding the family root of IL-17-producing cells. Nat Rev Immunol. Apr. 2006;6(4):329-33.
Dooms et al., Revisiting the role of IL-2 in autoimmunity. Eur J Immunol Jun. 2010;40(6):1538-40. doi: 10.1002/eji.201040617.
Duerr et al., A genome-wide association study identifies IL23R as an inflammatory bowel disease gene. Science. Dec. 1, 2006;314(5804):1461-3. Epub Oct. 26, 2006.
Eisenstein et al. Integration host factor is required for the DNA inversion that controls phase variation in *E. coli*. Proc Natl. Acad. Sci. 84, 6506-6510, 1987.
Elson, Commensal bacteria as targets in Crohn's disease. Gastroenterology. Jul. 2000;119(1):254-7.
Elson et al., Monoclonal anti-interleukin 23 reverses active colitis in a T cell-mediated model in mice. Gastroenterology. Jun. 2007;132(7):2359-70. Epub Apr. 13, 2007.
Falk et al., Creating and maintaining the gastrointestinal ecosystem: what we know and need to know from gnotobiology. Microbiol Mol Biol Rev. Dec. 1998;62(4):1157-70.
Feuerer et al., Foxp3+ regulatory T cells: differentiation, specification, subphenotypes. Nat Immunol. Jul. 2009;10(7):689-95. doi: 10.1038/ni.1760.
Finberg et al., Decay-accelerating factor expression on either effector or target cells inhibits cytotoxicity by human natural killer cells. J Immunol. Sep. 15, 1992;149(6):2055-60.
Fink et al., Human antigen-presenting cells respond differently to gut-derived probiotic bacteria but mediate similar strain-dependent NK and T cell activation. FEMS Immunol Med Microbiol. Dec. 2007;51(3):535-46. Epub Sep. 27, 2007.
Fontenot et al., Regulatory T cell lineage specification by the forkhead transcription factor foxp3. Immunity. Mar. 2005;22(3):329-41.
Fontenot et al., Foxp3 programs the development and function of CD4+CD25+ regulatory T cells. Nat Immunol Apr. 2003;4(4):330-6. Epub Mar. 3, 2003.
Fournier et al., Isolation of type 5 capsular polysaccharide from *Staphylococcus aureus*. Ann Inst Pasteur Microbiol. Sep.-Oct. 1987;138(5):561-7.
Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class II MHC molecules. Int Immunol. May 1999;11(5):635-41.
Fridkis-Hareli et al., Direct binding of myelin basic protein and synthetic copolymer 1 to class II major histocompatibility complex molecules on living antigen-presenting cells—specificity and promiscuity. Proc Natl Acad Sci U S A. May 24, 1994;91(11):4872-6.
Fridkis-Hareli et al., Synthetic copolymer 1 and myelin basic protein do not require processing prior to binding to class II major histocompatibility complex molecules on living antigen-presenting cells. Cell Immunol. Jul. 1995;163(2):229-36.
Froicu et al., A crucial role for the vitamin D receptor in experimental inflammatory bowel diseases. Mol Endocrinol. Dec. 2003;17(12):2386-92. Epub Sep. 18, 2003.
Froicu et al., Vitamin D receptor is required to control gastrointestinal immunity in IL-10 knockout mice. Immunology. Mar. 2006;117(3):310-8.
Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009.08.020.
Gally DL et al. Environmental regulation of the fim switch controlling type 1 fimbrial phase variation in *Escherichia coli* K-12: effects of temperature and media. (1993) J Bacteriol 175:6186-93.
Gelu-Simeon, et al., Evaluation and predictive factors of thyroid disorder due to interferon alpha in the treatment of hepatitis C. World J Gastroenterol 2009; 15(3):328-333.
Gerard et al., Interleukin 10 reduces the release of tumor necrosis factor and prevents lethality in experimental endotoxemia. J Exp Med. Feb. 1, 1993;177(2):547-50.
Gibson et al., Cellular mechanism of intraabdominal abscess formation by Bacteroides fragilis. J Immunol. May 15, 1998;160(10):5000-6.
Gibson et al., The capsular polysaccharide complex of Bacteroides fragilis induces cytokine production from human and murine phagocytic cells. Infect Immun. Mar. 1996;64(3):1065-9.
Gill et al., Metagenomic analysis of the human distal gut microbiome. Science. Jun. 2, 2006;312(5778):1355-9.
Glazebrook et al., A novel exopolysaccharide can function in place of the calcofluor-binding exopolysaccharide in nodulation of alfalfa by Rhizobium meliloti. Cell. Feb. 24, 1989;56(4):661-72.
Golgher et al., Galactofuranose-containing glycoconjugates of epimastigote and trypomastigote forms of Trypanosoma cruzi. Mol Biochem Parasitol. Aug. 1993;60(2):249-64.
Gondek et al., Cutting edge: contact-mediated suppression by CD4+CD25+ regulatory cells involves a granzyme B-dependent, perforin-independent mechanism. J Immunol. Feb. 15, 2005;174(4):1783-6.
Gonzalez-Hernandez et al., Peripheral blood CD161+ T cells from asthmatic patients are activated during asthma attack and predominantly produce IFN-gamma. Scand J Immunol Apr. 2007;65(4):368-75.
Goverman Autoimmune T cell responses in the central nervous system. Nat Rev Immunol. Jun. 2009;9(6):393-407. doi: 10.1038/nri2550.
Goverman et al., Transgenic mice that express a myelin basic protein-specific T cell receptor develop spontaneous autoimmunity. Cell. Feb. 26, 1993;72(4):551-60.
Grabow, Bacteriophages: Update on application as models for viruses in water. Water SA 2001;27(2):251-268.
Greenberger, P.A.; Drug allergy. J Allergy Clin Immunol 2006; 117(2):S464-S470.
Groux et al., A CD4+ T-cell subset inhibits antigen-specific T-cell responses and prevents colitis. Nature. Oct. 16, 1997;389(6652):737-42.
Groux et al., Type I T-regulatory cells: their role in the control of immune responses. Transplantation. May 15, 2003;75(9 Suppl):8S-12S.
Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall et al., Commensal DNA limits regulatory T cell conversion and is a natural adjuvant of intestinal immune responses. Immunity Oct. 17, 2008;29(4):637-49. doi: 10.1016/j.immuni.2008.08.009. Epub Oct. 2, 2008.
Hamelmann et al., Noninvasive measurement of airway responsiveness in allergic mice using barometric plethysmography. Am J Respir Crit Care Med. Sep. 1997;156(3 Pt 1):766-75.
Hampe et al., A genome-wide association scan of nonsynonymous SNPs identifies a susceptibility variant for Crohn disease in ATG16L1. Nat Genet. Feb. 2007;39(2):207-11. Epub Dec. 31, 2006.

(56) References Cited

OTHER PUBLICATIONS

Hampe et al., Association between insertion mutation in NOD2 gene and Crohn's disease in German and British populations. Lancet. Jun. 16, 2001;357(9272):1925-8.

Haregewoin et al., Human gamma delta+ T cells respond to mycobacterial heat-shock protein.Nature. Jul. 27, 1989;340(6231):309-12.

Harth et al. Treatment of mycobacterium tuberculosis with antisense oligonucleotides to glutamine synthetase mRNA inhibits glutamine synthetase activity, formation of poly-L-glutamate/glutamine cell wall structure, and bacterial replication. Proc Natl. Acad. Sci. 97: 418-423, 2000.

He et al., Intestinal bacteria trigger T cell-independent immunoglobulin A(2) class switching by inducing epithelial-cell secretion of the cytokine April. Immunity. Jun. 2007;26(6):812-26.

Hertl et al., T cell control in autoimmune bullous skin disorders. J Clin Invest. May 2006;116(5):1159-66. Review.

Hewison et al., Differential regulation of vitamin D receptor and its ligand in human monocyte-derived dendritic cells. J Immunol. Jun. 1, 2003;170(11):5382-90.

Hirata et al., Cytokine synthesis of human monocytes stimulated by triple or single helical conformer of an antitumour $(1\rightarrow 3)$-beta-D-glucan preparation, sonifilan. Zentralbl Bakteriol. Nov. 1998;288(3):403-13.

Hodge et al., Allium sativum (garlic) suppresses leukocyte inflammatory cytokine production in vitro: potential therapeutic use in the treatment of inflammatory bowel disease. Cytometry. Aug. 1, 2002;48(4):209-15.

Hofstetter et al., Th17 Cells in MS and Experimental Autoimmune Encephalomyelitis. Int MS J. Apr. 2009;16(1):12-8.

Hooper, Do symbiotic bacteria subvert host immunity? Nat Rev Microbiol. May 2009;7(5):367-74. doi: 10.1038/nrmicro2114.

Hooper et al., Commensal host-bacterial relationships in the gut. Science. May 11, 2001;292(5519):1115-8.

Hori et al., Control of regulatory T cell development by the transcription factor Foxp3. Science. Feb. 14, 2003;299(5609):1057-61. Epub Jan. 9, 2003.

Horstman et al., Enterotoxigenic *Escherichia coli* secretes active heat-labile enterotoxin via outer membrane vesicles. J Biol Chem. Apr. 28, 2000;275(17):12489-96.

Hue et al., Interleukin-23 drives innate and T cell-mediated intestinal inflammation. J Exp Med. Oct. 30, 2006;203(11):2473-83. Epub Oct. 9, 2006.

Huibregtse et al.., Immunopathogenesis of IBD: insufficient suppressor function in the gut? Gut. Apr. 2007;56(4):584-92. Epub Oct. 17, 2006.

Hutloff et al., ICOS is an inducible T-cell co-stimulator structurally and functionally related to CD28. Nature. Jan. 21, 1999;397(6716):263-6.

Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.

Ishikawa et al., Effect of intestinal microbiota on the induction of regulatory CD25+ CD4+ T cells. Clin Exp Immunol Jul. 2008;153(1):127-35. doi: 10.1111/j.1365-2249.2008.03668.x. Epub May 5, 2008.

Itokazu et al., Abscess formation as a complication caused by postoperative osteomyelitis of the femur. Arch Orthop Trauma Surg. 1998;118(1-2):99-102. Review.

Ivanov et al., Transcriptional regulation of Th17 cell differentiation. Semin Immunol. Dec. 2007;19(6):409-17. Epub Nov. 28, 2007.

Ivanov et al., The orphan nuclear receptor RORgammat directs the differentiation program of proinflammatory IL-17+ T helper cells. Cell. Sep. 22, 2006;126(6):1121-33.

Ivanov et al., Induction of intestinal Th17 cells by segmented filamentous bacteria. Cell. Oct. 30, 2009;139(3):485-98. doi: 10.1016/j.cell.2009.09.033.

Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.

Izcue et al., Regulatory T cells suppress systemic and mucosal immune activation to control intestinal inflammation. Immunol Rev. Aug. 2006;212:256-71.

Jeffery et al., 1,25-Dihydroxyvitamin D3 and IL-2 combine to inhibit T cell production of inflammatory cytokines and promote development of regulatory T cells expressing CTLA-4 and FoxP3. J Immunol. Nov. 1, 2009;183(9):5458-67. doi: 10.4049/jimmunol.0803217.

Jennings et al., Immunochemistry of groups A, B, and C meningococcal polysaccharide-tetanus toxoid conjugates. J Immunol. Sep. 1981;127(3):1011-8.

Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.

Jennings, H.J. et al., Structure of the Complex Polysaccharide C-Substance from *Streptococcus pneumoniae* Type 1; Biochem. 19:4712-4719 (1980).

Jia et al., Gut microbiota: a potential new territory for drug targeting. Nat Rev Drug Discov. Feb. 2008;7(2):123-9. doi: 10.1038/nrd2505.

Johnson et al., Bacterial capsular polysaccharide prevents the onset of asthma through T-cell activation. Glycobiology. Apr. 2015;25(4):368-75. doi: 10.1093/glycob/cwu117. Epub Oct. 27, 2014.

Jonuleit et al., Identification and functional characterization of human CD4(+)CD25(+) T cells with regulatory properties isolated from peripheral blood. J Exp Med. Jun. 4, 2001;193(11):1285-94.

Jonuleit et al., The regulatory T cell family: distinct subsets and their interrelations. J Immunol. Dec. 15, 2003;171(12):6323-7.

Joshi et al., 1,25-dihydroxyvitamin D(3) ameliorates Th17 autoimmunity via transcriptional modulation of interleukin-17A. Mol Cell Biol. Sep. 2011;31(17):3653-69. doi: 10.1128/MCB.05020-11. Epub Jul. 11, 2011.

Jotwani et al., Pathogenicity of Bacteroides fragilis group in rat intra-abdominal abscesses. Microbiol Immunol. 1992;36(10):1041-9.

Jyonouchi, H.; Non-IgE Mediated Food Allergy; Inflammation & Allergy—Drug Targets 2008; 7(3):1-8.

Kakalacheva et al., Viral triggers of multiple sclerosis. Biochim Biophys Acta. Feb. 2011;1812(2):132-40. doi: 10.1016/j.bbadis.2010.06.012. Epub Jun. 25, 2010.

Kakalacheva et al., Environmental triggers of multiple sclerosis. FEBS Lett. Dec. 1, 2011;585(23):3724-9. doi: 10.1016/j.febslet.2011.04.006. Epub Apr. 7, 2011.

Kalka-Moll et al., Bacteriodes Fragilis NCTC 9343 Capsular Polysaccharide PS A and the Effect of Chain Length of T cell Proliferation. Abstracts of the 98th Gen Mtg of the American Soc for Microbiol. 1998;98:123. Abstract B-405.

Kalka-Moll et al., Immunochemical and biological characterization of three capsular polysaccharides from a single Bacteroides fragilis strain. Infect Immun. Apr. 2001;69(4):2339-44.

Kalka-Moll et al.,Effect of molecular size on the ability of zwitterionic polysaccharides to stimulate cellular immunity. J Immunol. Jan. 15, 2000;164(2):719-24.

Kalka-Moll, et al., Zwitterionic Polysaccharides Stimulate T Cells by MHC Class II-Dependent Interactions; J. Immunol.; 2002;169: 6149-6153.

Kasper et al., Capsular polysaccharides and lipopolysaccharides from two Bacteroides fragilis reference strains: chemical and immunochemical characterization. J Bacteriol. Feb. 1983;153(2):991-7.

Kasper et al., Protective efficacy of immunization with capsular antigen against experimental infection with Bacteroides fragilis. J Infect Dis. Nov. 1979;140(5):724-31.

Kasper et al., Surface antigens as virulence factors in infection with Bacteroides fragilis. Rev.Infect Dis. Mar.-Apr. 1979;1(2):278-90.

(56) References Cited

OTHER PUBLICATIONS

Kasper et al., The polysaccharide capsule of Bacteroides fragilis subspecies fragilis: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kenne et al., Structural studies of the O-specific side-chains of the Shigella sonnei phase I lipopolysaccharide. Carbohydrate Res. 1980;78:119-126.
Kennedy et al., Prevention of experimental postoperative peritoneal adhesions by N,O-carboxymethyl chitosan. Surgery. Nov. 1996;120(5):866-70.
Kernodle et al. Expression of an antisense hla fragment in *Staphylococcus aureus* reduces alpha-toxin production in vitro and attenuates lethal activity in a murine model. Infection and Immunity 179-184. 1997.
Kesty et al., Incorporation of heterologous outer membrane and periplasmic proteins into *Escherichia coli* outer membrane vesicles. J Biol Chem. Jan. 16, 2004;279(3):2069-76. Epub Oct. 24, 2003.
Kidd, Th1/Th2 balance: the hypothesis, its limitations, and implications for health and disease. Altern Med Rev. Aug. 2003;8(3):223-46.
Kim et al., Regulatory T cells prevent catastrophic autoimmunity throughout the lifespan of mice. Nat Immunol. Feb. 2007;8(2):191-7. Epub Nov. 30, 2006.
Kinoshita et al., Retinoic acid reduces autoimmune renal injury and increases survival in NZB/W F1 mice. J Immunol. Jun. 1, 2003;170(11):5793-8.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of O-specific polysaccharide chains of lipopolysaccharides of P. aeruginosa O3 (Lanyi), O25 (Wokatsch) and Fisher immunotypes 3 and 7. Eur J Biochem. Sep. 15, 1987;167(3):549-61.
Knirel et al., The structure of O-specific polysaccharides and serological classification of Pseudomonas aeruginosa (a review). Acta Microbiol Hung. 1988;35(1):3-24. Review.
Koch et al., The transcription factor T-bet controls regulatory T cell homeostasis and function during type 1 inflammation. Nat Immunol. Jun. 2009;10(6):595-602. doi: 10.1038/ni.1731. Epub May 3, 2009.
Kong et al., Novel role of the vitamin D receptor in maintaining the integrity of the intestinal mucosal barrier. Am J Physiol Gastrointest Liver Physiol. Jan. 2008;294(1):G208-16. Epub Oct. 25, 2007.
Kormelink, T.G., et al.; Atopic and non-atopic allergic disorders: current insights into the possible involvement of free immunoglobulin light chains; Clinical and Experimental Allergy 2008; 39:33-42.
Krinos et al., Extensive surface diversity of a commensal microorganism by multiple DNA inversions. (2001) Nature 414:555-8.
Krutzik et al., IL-15 links TLR2/1-induced macrophage differentiation to the vitamin D-dependent antimicrobial pathway. J Immunol Nov. 15, 2008;181(10):7115-20.
Kuehn et al., Bacterial outer membrane vesicles and the host-pathogen interaction. Genes Dev. Nov. 15, 2005;19(22):2645-55.
Kuhn et al., Interleukin-10-deficient mice develop chronic enterocolitis. Cell. Oct. 22, 1993;75(2):263-74.
Kulberg et al., Bacteria-triggered CD4(+) T regulatory cells suppress Helicobacter hepaticus-induced colitis. J Exp Med. Aug. 19, 2002;196(4):505-15.
Kulberg et al., IL-23 plays a key role in Helicobacter hepaticus-induced T cell-dependent colitis. J Exp Med. Oct. 30, 2006;203(11):2485-94. Epub Oct. 9, 2006.
Kulberg et al., Induction of colitis by a CD4+ T cell clone specific for a bacterial epitope. Proc.Natl Acad Sci U S A. Dec. 23, 2003;100(26):15830-5. Epub Dec. 12, 2003.
Kulberg et al., Helicobacter hepaticus triggers colitis in specific-pathogen-free interleukin-10 (IL-10)-deficient mice through an IL-12- and gamma interferon-dependent mechanism. Infect Immun. Nov. 1998;66(11):5157-66.
Kulicke et al., Correlation between immunological activity, molar mass, and molecular structure of different (1-->3)-beta-D-glucans. Carbohydr Res. Jan. 2, 1997;297(2):135-43.
Kurup et al., Antibody response to low-molecular-weight antigens of Aspergillus fumigatus in allergic bronchopulmonary aspergillosis. J Clin Microbiol. Jun. 1989;27(6):1312-6.
Lagishetty et al., Vitamin D deficiency in mice impairs colonic antibacterial activity and predisposes to colitis. Endocrinology. Jun. 2010;151(6):2423-32. doi: 10.1210/en.2010-0089. Epub Apr. 14, 2010.
Lee et al., Proinflammatory T-cell responses to gut microbiota promote experimental autoimmune encephalomyelitis. Proc Natl Acad Sci U S A. Mar. 15, 2011;108 Suppl 1:4615-22. doi: 10.1073/pnas.1000082107. Epub Jul. 26, 2010.
Lee et al., Has the microbiota played a critical role in the evolution of the adaptive immune system? Science. Dec. 24, 2010;330(6012):1768-73. doi: 10.1126/science.1195568.
Lee et al., Effects of In Vitro and In Vivo and Growth Conditions on Expression of Type 8 Capsular Polysaccharide by *Staphylococcus aureus*, Infection and Immunity, 61:1853-1858, 1993.
Ley et al., Ecological and evolutionary forces shaping microbial diversity in the human intestine. Cell. Feb. 24, 2006;124(4):837-48.
Lin et al., Regulatory T cell development in the absence of functional Foxp3. Nat Immunol. Apr. 2007;8(4):359-68. Epub Feb. 2, 2007.
Lindberg et al., Structural Studies of the Capsular Polysaccharide from *Streptococcus pneumoniae* Type 1; Carbohydrate Res 78:111-117 (1980).
Liu et al., Altered endocrine and autocrine metabolism of vitamin D in a mouse model of gastrointestinal inflammation. Endocrinology. Oct. 2008;149(10):4799-808. doi: 10.1210/en.2008-0060. Epub Jun. 5, 2008.
Liu et al., Toll-like receptor 2 signaling modulates the functions of CD4+ CD25+ regulatory T cells. Proc Natl Acad Sci U S A. May 2, 2006;103(18):7048-53. Epub Apr. 21, 2006.
Liu et al., Regulation of surface architecture by symbiotic bacteria mediates host colonization. Proc Natl Acad Sci U S A. Mar. 11, 2008;105(10):3951-6. doi: 10.1073/pnas.0709266105. Epub Mar. 4, 2008.
Liu et al., Toll-like receptor triggering of a vitamin D-mediated human antimicrobial response. Science. Mar. 24, 2006;311(5768):1770-3. Epub Feb. 23, 2006.
Lysnyansky et al. Juxtaposition of an active promoter to vsp genes via site-specific DNA inversions generates antigenic variation in Mycoplasma bovis. (2001) J Bacteriol 183:5698-5708.
Maconi et al., Contrast radiology, computed tomography, and ultrasonography in detecting internal fistulas and intra-abdominal abscesses in Chrohn's disease: a prospective comparative study. Amer J Gast. 2003;98(7):1545-1555.
MacPherson et al., Mucosal antibodies in inflammatory bowel disease are directed against intestinal bacteria. Gut. Mar. 1996;38(3):365-75.
MacPherson et al., Induction of protective IgA by intestinal dendritic cells carrying commensal bacteria. Science. Mar. 12, 2004;303(5664):1662-5.
Maier et al., Experimental Shigella infections in laboratory animals. I. Antagonism by human normal flora components in gnotobiotic mice. Infect Immun. Aug. 1972;6(2):168-73.
Makela et al., IL-10 is necessary for the expression of airway hyperresponsiveness but not pulmonary inflammation after allergic sensitization. Proc Natl Acad Sci U S A. May 23, 2000;97(11):6007-12.
Maloy et al., CD4+CD25+ T(R) cells suppress innate immune pathology through cytokine-dependent mechanisms. J Exp Med. Jan. 6, 2003;197(1):111-9.
Maynard et al., Diversity in the contribution of interleukin-10 to T-cell-mediated immune regulation. Immunol Rev. Dec. 2008;226:219-33. doi: 10.1111/j.1600-065X.2008.00711.x.
Maynard et al., Contrasting roles for all-trans retinoic acid in TGF-beta-mediated induction of Foxp3 and Il10 genes in developing regulatory T cells. J Exp Med. Feb. 16, 2009;206(2):343-57. doi: 10.1084/jem.20080950. Epub Feb. 9, 2009.

(56) References Cited

OTHER PUBLICATIONS

Maynard et al., Regulatory T cells expressing interleukin 10 develop from Foxp3+ and Foxp3-precursor cells in the absence of interleukin 10. Nat Immunol Sep. 2007;8(9):931-41. Epub Aug. 12, 2007.
Mayne et al., 1,25-Dihydroxyvitamin D3 acts directly on the T lymphocyte vitamin D receptor to inhibit experimental autoimmune encephalomyelitis. Eur J Immunol. Mar. 2011;41(3):822-32. doi: 10.1002/eji.201040632. Epub Feb. 1, 2011.
Mazmanian et al., An immunomodulatory molecule of symbiotic bacteria directs maturation of the host immune system. Cell. Jul. 15, 2005;122(1):107-18.
Mazmanian et al., The love-hate relationship between bacterial polysaccharides and the host immune system. Nature Reviews Immunology. 2006;6: 849-858.
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01.mpg.0000313824.70971.a7.
McClain et al. Inversion-independent phase variation of type 1 fimbriae in *Escherichia coli*. (1993) J Bacteriol 175(14):4335-44.
McMurchy et al., Suppression assays with human T regulatory cells: a technical guide. Eur J Immunol. Jan. 2012;42(1):27-34. doi: 10.1002/eji.201141651. Epub Dec. 12, 2011.
Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41(2):129-31.
Mertens et al., *Streptococcus pneumoniae* serotype 1 capsular polysaccharide induces CD8 CD28 regulatory T lymphocytes by TCR crosslinking. PLoS Pathog. Sep. 2009;5(9):e1000596. doi: 10.1371/journal.ppat.1000596. Epub Sep. 25, 2009.
Miller et al., Severe asthma and the omalizumab option. Clinical and Molecular Allergy 2008, 6:4.
Min et al., Gut flora antigens are not important in the maintenance of regulatory T cell heterogeneity and homeostasis. Eur J Immunol. Jul. 2007;37(7):1916-23.
Mojtabavi et al., Long-lived Th2 memory in experimental allergic asthma. J Immunol. Nov. 1, 2002;169(9):4788-96.
Montz et al., Interleukin 10: ability to minimize postoperative intraperitoneal adhesion formation in a murine model. Fertil Steril. Jun. 1994;61(6):1136-40.
Moore, The List Goes On, New Additions to the Autoimmune Disease Roster. http://autoimmunedisease.suite101.com/blog.cfm/the_list_goes_on. pp. 1-3.
Mor et al., Identification of aldolase as a target antigen in Alzheimer's disease. J Immunol. Sep. 1, 2005;175(5):3439-45.
Mora et al., Generation of gut-homing IgA-secreting B cells by intestinal dendritic cells. Science. Nov. 17, 2006;314(5802):1157-60.
Mora et al., Selective imprinting of gut-homing T cells by Peyer's patch dendritic cells. Nature. Jul. 3, 2003;424(6944):88-93.
Morales-Tirado et al., 1α,25-dihydroxyvitamin D3 (vitamin D3) catalyzes suppressive activity on human natural regulatory T cells, uniquely modulates cell cycle progression, and augments FOXP3. Clin Immunol. Feb. 2011;138(2):212-21. doi: 10.1016/j.clim.2010.11.003. Epub Dec. 16, 2010.
Mulholland et al., Strategies for the control of pneumococcal diseases. Vaccine. Jul. 30, 1999;17 Suppl 1:S79-84. Review.
Nakayama-Imaohji et al., Identification of the site-specific DNA invertase responsible for the phase variation of SusC/SusD family outer membrane proteins in Bacteroides fragilis. J Bacteriol. Oct. 2009;191(19):6003-11. doi: 10.1128/JB.00687-09. Epub Jul. 31, 2009.
Natori et al., Agelasphins, novel antitumor and immunostimulatory cerebrosides from the marine sponge Agelas mauritianus. Tetrahedron. 1994;50(9):2771-2784.
NCBI Sequence View "Toxin" [*Salmonella typhimurium* LT2]. http://www.ncbi.nlm.nih.gov/entrez/viewer.fcgi?db=protein&id=17233414, pp. 1-2.

Neurath et al., TNBS-colitis. Int Rev Immunol. 2000;19(1):51-62.
Nielsen et al., Applications of peptide nucleic acids. Curr Opin Biotechnol. Feb. 1999;10(1):71-5. Review.
Niess et al., Commensal gut flora drives the expansion of proinflammatory CD4 T cells in the colonic lamina propria under normal and inflammatory conditions. J Immunol. Jan. 1, 2008;180(1):559-68.
Norman; "Thyroiditis—Inflammation of the thyroid gland"; Endocrineweb 2009; www.endocrineweb.com/throiditis.html, 1-4. Downloaded Jul. 28, 2009.
Noverr et al., Does the microbiota regulate immune responses outside the gut? Trends Microbiol. Dec. 2004;12(12):562-8.
Nylander et al., Multiple sclerosis. J Clin Invest. Apr. 2012;122(4):1180-8. doi: 10.1172/JCI58649. Epub Apr. 2, 2012.
O'Connor et al., Translational mini-review series on Th17 cells: CD4 T helper cells: functional plasticity and differential sensitivity to regulatory T cell-mediated regulation. Clin Exp Immunol. Feb. 2010;159(2):137-47. doi: 10.1111/j.1365-2249.2009.04040.x. Epub Nov. 11, 2009.
O'Garra et al., IL-10-producing and naturally occurring CD4+ Tregs: limiting collateral damage. J Clin Invest. Nov. 2004;114(10):1372-8.
O'Hara et al., The gut flora as a forgotten organ. EMBO Rep. Jul. 2006;7(7):688-93.
Ochoa-Reparaz et al., Central nervous system demyelinating disease protection by the human commensal Bacteroides fragilis depends on polysaccharide A expression. J Immunol. Oct. 1, 2010;185(7):4101-8. doi: 10.4049/jimmuno1.1001443. Epub Sep. 3, 2010.
Ochoa-Reparaz et al., Role of gut commensal microflora in the development of experimental autoimmune encephalomyelitis. J Immunol. Nov. 15, 2009;183(10):6041-50. doi: 10.4049/jimmunol.0900747. Epub Oct. 19, 2009.
Oda et al., A comprehensive map of the toll-like receptor signaling network. Mol Syst Biol. 2006;2:2006.0015. Epub Apr. 18, 2006.
Oh et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1-->3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk, A. et al., Evidence for T Cell-dependent Immunity to Bacteroides fragilis in an Intraabdominal Abscess Model; J. Clin Invest. 69:9-16 (1982).
Ostman et al., Impaired regulatory T cell function in germ-free mice. Eur J Immunol. Sep. 2006;36(9):2336-46.
Ozenci et al., Multiple sclerosis: levels of interleukin-10-secreting blood mononuclear cells are low in untreated patients but augmented during interferon-beta-1b treatment. Scand J Immunol. May 1999;49(5):554-61.
Palmer et al., Lineage-specific effects of 1,25-dihydroxyvitamin D(3) on the development of effector CD4 T cells. J Biol Chem. Jan. 14, 2011;286(2):997-1004. doi: 10.1074/jbc.M110.163790. Epub Nov. 3, 2010.
Palmer et al., Development of the human infant intestinal microbiota. PLoS Biol. Jul. 2007;5(7):e177. Epub Jun. 26, 2007.
Pamer, Immune responses to commensal and environmental microbes. Nat Immunol. Nov. 2007;8(11):1173-8.
Pantosti et al., Bacteroides fragilis strains express multiple capsular polysaccharides. J Clin Microbiol. Jul. 1993;31(7):1850-5.
Paoletti et al., Neonatal Mouse Protection against Infection with Multiple Group B Streptococcal (GBS) Serotypes by Maternal Immunization with a Tetravalent GBS Polysaccharide-Tetanus Toxoid Conjugate Vaccine, Infection and Immunity, 62:3236-3243, 1994.

(56) References Cited

OTHER PUBLICATIONS

Paoletti et al., Effects of chain length on the immunogenicity in rabbits of group B *Streptococcus* type III oligosaccharide-tetanus toxoid conjugates. J Clin Invest. Jan. 1992;89(1):203-9.
Park et al., Interleukin-2 and soluble interleukin-2 receptor in bronchoalveolar lavage fluid from patients with bronchial asthma. Chest. Aug. 1994;106(2):400-6.
Patrick et al., Separation of capsulate and non-capsulate Bacteroides fragilis on a discontinuous density gradient. J Med Microbiol. May 1983;16(2):239-41.
Patrick et al., A comparison of the haemagglutinating and enzymic activities of Bacteroides fragilis whole cells and outer membrane vesicles. Microb Pathog. Apr. 1996;20(4):191-202.
Patrick et al., Mutational analysis of genes implicated in LPS and capsular polysaccharide biosynthesis in the opportunistic pathogen Bacteroides fragilis. Microbiology. Apr. 2009;155(Pt.4):1039-49. doi: 10.1099/mic.0.025361-0.
Pavliak et al., Structural elucidation of the capsular polysaccharide of Bacteroides fragilis strain 23745M1. Carbohydr Res. Oct. 2, 1995;275(2):333-41.
Pedersen et al., 1,25-dihydroxyvitamin D3 reverses experimental autoimmune encephalomyelitis by inhibiting chemokine synthesis and monocyte trafficking. J Neurosci Res. Aug. 15, 2007;85(11):2480-90.
Perumal et al., Protective effect of interleukin-2 on experimental intra-abdominal abscess development due to Bacteriodes Fragilis. Clinical Research. 1990;38(2):550A.
Pierrot-Deseilligny et al., Is hypovitaminosis D one of the environmental risk factors for multiple sclerosis? Brain. Jul. 2010;133(Pt 7):1869-88. doi: 10.1093/brain/awq147.
Poonawalla et al.; Urticaria a Review; Am J Clin Dermotol 2009; 10(1):9-21.
Popovic et al., Inhibition of autoimmune encephalomyelitis by a tetracycline. Ann Neurol. Feb. 2002;51(2):215-23.
Powrie et al., Immunology. Regulating the regulators. Science. Feb. 14, 2003;299(5609):1030-1.
Poxton et al., Mucosa-associated bacterial flora of the human colon. J Med Microbiol. Jan. 1997;46(1):85-91.
Prieto et al., A New Ganglioside in Human Meconium Detected by Antiserum against the Human Milk Sialyloligosaccharide, LS-Tetrasaccharide b.sup.1, Archives of Biochemistry and Biophysics, 241:281-289, 1985.
Rabe et al., Pharmacological treatment of asthma today. Eur Respir J Suppl. 2001;34:34s-40s.
Raghuwanshi et al., Vitamin D and multiple sclerosis. J Cell Biochem. Oct. 1, 2008;105(2):338-43. doi: 10.1002/jcb.21858.
Rakoff-Nahoum et al., Recognition of commensal microflora by toll-like receptors is required for intestinal homeostasis. Cell. Jul. 23, 2004;118(2):229-41.
Raman et al., Vitamin D and gastrointestinal diseases: inflammatory bowel disease and colorectal cancer. Therap Adv Gastroenterol. Jan. 2011;4(1):49-62. doi: 10.1177/1756283X10377820.
Ranua et al., Serum IgA, IgG, and IgM concentrations in patients with epilepsy and matched controls: a cohort-based cross-sectional study. Epilepsy Behav. Mar. 2005;6(2):191-5.
Reed et al., A simple method of estimating fifty percent endpoints. Am J Hyg. 1938;27:493-497.
Rescigno et al., Dendritic cells express tight junction proteins and penetrate gut epithelial monolayers to sample bacteria. Nat Immunol. Apr. 2001;2(4):361-7.
Riesenfeld et al., Biosynthesis of heparin. Assay and properties of the microsomal N-acetyl-D-glucosaminyl N-deacetylase.J Biol Chem. Feb. 10, 1980;255(3):922-8.
Roncarolo et al., Type I T regulatory cells. Immunol Rev. Aug. 2001;182:68-79. Review.
Round et al., Coordination of tolerogenic immune responses by the commensal microbiota. J Autoimmun. May 2010;34(3):J220-5. doi: 10.1016/j.jaut.2009.11.007. Epub Dec. 6, 2009.
Round et al., The Toll-like receptor 2 pathway establishes colonization by a commensal of the human microbiota. Science. May 20, 2011;332(6032):974-7. doi: 10.1126/science.1206095. Epub Apr. 21, 2011.
Round et al., The gut microbiota shapes intestinal immune responses during health and disease. Nat Rev Immunol. May 2009;9(5):313-23. doi: 10.1038/nri2515.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Rubtsov et al., Regulatory T cell-derived interleukin-10 limits inflammation at environmental interfaces. Immunity. Apr. 2008;28(4):546-58. doi: 10.1016/j.immuni.2008.02.017.
Runia et al., Lower serum vitamin D levels are associated with a higher relapse risk in multiple sclerosis. Neurology. Jul. 17, 2012;79(3):261-6. doi: 10.1212/WNL.0b013e31825fdec7. Epub Jun. 13, 2012.
Rutgeerts et al., Infliximab for induction and maintenance therapy for ulcerative colitis. N Engl J Med. Dec. 8, 2005;353(23):2462-76.
Rypens et al., Percutaneous drainage of abdominal abscesses in pediatric Crohn's disease. AJR Am J Roentgenol. Feb. 2007;188(2):579-85.
Sakaguchi et al., Regulatory T cells and immune tolerance. Cell. May 30, 2008;133(5):775-87. doi: 10.1016/j.cell.2008.05.009.
Sakaguchi et al., Foxp3+ CD25+ CD4+ natural regulatory T cells in dominant self-tolerance and autoimmune disease. Immunol Rev. Aug. 2006;212:8-27.
Salyers et al., Conjugative transposons: an unusual and diverse set of integrated gene transfer elements. Microbiol Rev. Dec. 1995;59(4):579-90. Review.
Sartor, Mechanisms of disease: pathogenesis of Crohn's disease and ulcerative colitis. Nat Clin Pract Gastroenterol Hepatol. Jul. 2006;3(7):390-407.
Sawada et al., Leukocytapheresis in ulcerative colitis: results of a multicenter double-blind prospective case-control study with sham apheresis as placebo treatment. Am J Gastroenterol. Jun. 2005;100(6):1362-9.
Scheiffele et al., Induction of TNBS colitis in mice. Curr Protoc Immunol. Aug. 2002;Chapter 15:Unit 15.19. doi: 10.1002/0471142735.im1519s49.
Scheinin et al., Validation of the interleukin-10 knockout mouse model of colitis: antitumour necrosis factor-antibodies suppress the progression of colitis. Clin Exp Immunol. Jul. 2003;133(1):38-43.
Schembri MA et al. Orientation-dependent enhancement by H-NS of the activity of the type 1 fimbrial phase switch promoter in *Escherichia coli*. (1998) Mol Gen Genet 259:336-44.
Schlegel et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. Proc Natl Acad Sci U S A. May 14, 1996;93(10):5061-6. Erratum in: Proc Natl Acad Sci U S A Aug. 6, 1996;93(16):8796.
Schneider et al., De novo design of molecular architectures by evolutionary assembly of drug-derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.
Sellon et al., Resident enteric bacteria are necessary for development of spontaneous colitis and immune system activation in interleukin-10-deficient mice. Infect Immun. Nov. 1998;66(11):5224-31.
Shaklee et al., Hydrazinolysis of heparin and other glycosaminoglycans. Biochem. J. (1984); 217: 187-197.
Shapiro et al., Cellular control of abscess formation: role of T cells in the regulation of abscesses formed in response to Bacteroides fragilis. J Immunol. Jul. 1, 1986;137(1):341-6.

(56) References Cited

OTHER PUBLICATIONS

Shapiro et al., Cellular immunity to Bacteroides fragilis capsular polysaccharide. J Exp Med. Apr. 1, 1982;155(4):1188-97.
Sharpe et al., The B7-CD28 superfamily. Nat Rev Immunol. Feb. 2002;2(2):116-26. Review.
Shevach, CD4+ CD25+ suppressor T cells: more questions than answers. Nat Rev Immunol. Jun. 2002;2(6):389-400. Review.
Sigmundsdottir et al., DCs metabolize sunlight-induced vitamin D3 to 'program' T cell attraction to the epidermal chemokine CCL27. Nat Immunol. Mar. 2007;8(3):285-93. Epub Jan. 28, 2007.
Silvestro et al., Effects of subinhibitory concentrations of clindamycin on the morphological, biochemical and genetic characteristics of Bacteroides fragilis. FEMS Microbiol Lett. Apr. 2006;257(2):189-94.
Simmons et al., Synthesis and membrane permeability of PNA-peptide conjugates. Bioorg Med Chem Lett. 1997;7(23):3001-6.
Slack et al., Innate and adaptive immunity cooperate flexibly to maintain host-microbiota mutualism. Science. Jul. 31, 2009;325(5940):617-20. doi: 10.1126/science.1172747.
Smith SG et al. Functional analysis of the FimE integrase of *Escherichia coli* K-12: isolation of mutant derivatives with altered DNA inversion preferences. (1999) Mol Microbiol 34:965-79.
Smith et al., Use of axenic animals in studying the adaptation of mammals to their commensal intestinal microbiota. Semin Immunol. Apr. 2007;19(2):59-69. Epub Nov. 21, 2006.
Smits et al., Selective probiotic bacteria induce IL-10-producing regulatory T cells in vitro by modulating dendritic cell function through dendritic cell-specific intercellular adhesion molecule 3-grabbing nonintegrin. J Allergy Clin Immunol. Jun. 2005;115(6):1260-7.
Solomon et al., Multiple sclerosis and vitamin D: a review and recommendations. Curr Neurol Neurosci Rep. Sep. 2010;10(5):389-96. doi: 10.1007/s11910-010-0131-5.
Spach et al., Vitamin D3 confers protection from autoimmune encephalomyelitis only in female mice. J Immunol. Sep. 15, 2005;175(6):4119-26.
Spach et al., Gene expression analysis suggests that 1,25-dihydroxyvitamin D3 reverses experimental autoimmune encephalomyelitis by stimulating inflammatory cell apoptosis. Physiol Genomics. Jul. 8, 2004;18(2):141-51.
Sprinz et al., The response of the germfree guinea pig to oral bacterial challenge with *Escherichia coli* and *Shigella flexneri*. Am J Pathol. Dec. 1961;39:681-95.
Stein et al., Thymus-independent and thymus-dependent responses to polysaccharide antigens. J Infect Dis. Jun. 1992;165 Suppl 1:S49-52. Review.
Stewart et al., Interferon-β and serum 25-hydroxyvitamin D interact to modulate relapse risk in MS. Neurology. Jul. 17, 2012;79(3):254-60. doi: 10.1212/WNL.0b013e31825fded9. Epub Jun. 13, 2012.
Stingele et al., Zwitterionic polysaccharides stimulate T cells with no preferential V beta usage and promote anergy, resulting in protection against experimental abscess formation. J Immunol. Feb. 1, 2004;172(3):1483-90.
Stockinger et al., Differentiation and function of Th17 T cells. Curr Opin Immunol. Jun. 2007;19(3):281-6. Epub Apr. 12, 2007.
Strachan, Hay fever, hygiene, and household size. BMJ. Nov. 18, 1989;299(6710):1259-60.
Strauch et al., Influence of intestinal bacteria on induction of regulatory T cells: lessons from a transfer model of colitis. Gut. Nov. 2005;54(11):1546-52. Epub Jun. 29, 2005.
Strober, The multifaceted influence of the mucosal microflora on mucosal dendritic cell responses. Immunity Sep. 18, 2009;31(3):377-88. doi: 10.1016/j.immuni.2009.09.001.
Stromnes et al., Active induction of experimental allergic encephalomyelitis. Nat Protoc. 2006;1(4):1810-9.
Stromnes et al., Passive induction of experimental allergic encephalomyelitis. Nat Protoc. 2006;1(4):1952-60.
Stumhofer et al., Interleukins 27 and 6 induce STAT3-mediated T cell production of interleukin 10. Nat Immunol. Dec. 2007;8(12):1363-71. Epub Nov. 11, 2007.
Suri-Payer et al., CD4+CD25+ T cells inhibit both the induction and effector function of autoreactive T cells and represent a unique lineage of immunoregulatory cells. J Immunol. Feb. 1, 1998;160(3):1212-8.
Sutmuller et al., Toll-like receptor 2 controls expansion and function of regulatory T cells. J Clin Invest. Feb. 2006;116(2):485-94. Epub Jan. 19, 2006.
Szu et al., Relation between structure and immunologic properties of the Vi capsular polysaccharide. Infect Immun. Dec. 1991;59(12):4555-61.
Tanaka et al., Human monocyte-derived dendritic cells induce naive T cell differentiation into T helper cell type 2 (Th2) or Th1/Th2 effectors. Role of stimulator/responder ratio. J Exp Med. Aug. 7, 2000;192(3):405-12.
Tang et al., Th type 1-stimulating activity of lung macrophages inhibits Th2-mediated allergic airway inflammation by an IFN-gamma-dependent mechanism. J Immunol. Feb. 1, 2001;166(3):1471-81.
Taurog et al., The germfree state prevents development of gut and joint inflammatory disease in HLA-B27 transgenic rats. J Exp Med. Dec. 1, 1994;180(6):2359-64.
Taylor et al., Stoichiometric depolymerization of polyuronides and glycosaminoglycuronans to monosaccharides following reduction of their carbodiimide-activated carboxyl groups. Biochemistry. Apr. 11, 1972;11(8):1383-8.
Teitelbaum et al., Immunomodulation of experimental autoimmune encephalomyelitis by oral administration of copolymer 1. Proc Natl Acad Sci U S A. Mar. 30, 1999;96(7):3842-7.
Teitelbaum et al., Specific inhibition of the T-cell response to myelin basic protein by the synthetic copolymer Cop 1. Proc Natl Acad Sci U S A. Dec. 1988;85(24):9724-8.
Teitelbaum et al., Synthetic copolymer 1 inhibits human T-cell lines specific for myelin basic protein. Proc Natl Acad Sci U S A. Jan. 1, 1992;89(1):137-41.
Teitelbaum et al., Unprimed spleen cell populations recognize macrophage-bound antigen with opposite net electric charge. Proc Natl Acad Sci U S A. Apr. 1977;74(4):1693-6.
Thomas et al., Randomized controlled trial of short bursts of a potent topical corticosteroid versus prolonged use of a mild preparation for children with mild or moderate atopic eczema. BMJ. 2002;324:1-7.
Tournoy et al., Endogenous interleukin-10 suppresses allergen-induced airway inflammation and nonspecific airway responsiveness. Clin Exp Allergy. Jun. 2000;30(6):775-83.
Toussirot et al., Bacterial extract (OM-89) specific and non specific immunomodulation in rheumatoid arthritis patients. Autoimmunity. Jun. 2006;39(4):299-306.
Troy et al., Beneficial effects of Bacteroides fragilis polysaccharides on the immune system. Front Biosci (Landmark Ed). Jan. 1, 2010;15:25-34.
Troy et al., Orientations of the Bacteroides fragilis capsular polysaccharide biosynthesis locus promoters during symbiosis and infection. J Bacteriol. Nov. 2010;192(21):5832-6. doi: 10.1128/JB.00555-10. Epub Aug. 20, 2010.
Turnbaugh et al., The human microbiome project. Nature. Oct. 18, 2007;449(7164):804-10.
Turnbaugh et al., An obesity-associated gut microbiome with increased capacity for energy harvest. Nature. Dec. 21, 2006;444(7122):1027-31.
Tzianabos, A.O., Polysaccharide Immunomodulators as Therapeutic Agents: Structural Aspects and Biologic Function, Clin. Microbiol. Rev. 13(4):523-533 (2000).
Tzianabos, AO et al., Polysaccharide-mediated protection against abscess formation in experimental intra-abdominal sepsis. J Clin. Invest. (1995) 96:2727-31.
Tzianabos, AO et al., Structural characteristics of polysaccharides that induce protection against intra-abdominal abscess formation. Infect Immun (1994) 62:4881-86.
Tzianabos et al., Bacterial structure and functional relation to abscess formation. Infect Agents Dis. Oct. 1994;3(5):256-65. Review.

(56) References Cited

OTHER PUBLICATIONS

Tzianabos et al., Characteristics of bacterial polysaccharides that activate T cells. The International Carbohydrate Symposium XVII. Jul. 21, 1994.

Tzianabos et al., Effect of surgical adhesion reduction devices on the propagation of experimental intra-abdominal infection. Arch Surg. Nov. 1999;134(11):1254-9.

Tzianabos et al., IL-2 mediates protection against abscess formation in an experimental model of sepsis. J Immunol. Jul. 15, 1999;163(2):893-7.

Tzianabos et al., Protection against experimental intraabdominal sepsis by two polysaccharide immunomodulators. J Infect Dis. Jul. 1998;178(1):200-6.

Tzianabos et al., Structural basis for polysaccharide-mediated protection against intraabdominal abscess formation. 94$^{th}$ ASM General Meeting. May 23-27, 1994. Las Vegas, Nevada. Abstract B-206:65.

Tzianabos, et al., Structural rationale for the modulation of abscess formation by Staphylococcus aureus capsular polysaccharides. Proc Natl Acad Sci U S A. Jul. 31, 2001;98(16):9365-70. Epub Jul. 24, 2001.

Tzianabos et al., Structure and function of Bacteroides fragilis capsular polysaccharides: relationship to induction and prevention of abscesses. Clin Infect Dis. Jun. 1995;20 Suppl 2:S132-40. Review.

Tzianabos et al., Structure-function relationships for polysaccharide-induced intra-abdominal abscesses. Infect Immun. Aug. 1994;62(8):3590-3.

Tzianabos et al., T Cell Activation by Zwitterionic polysaccharides and peptide mimetics prevents antrabdominal abscess formation. Abstracts of the 99$^{th}$ General Meeting of the American Society for Microbiology. Chicago, US: May 30-Jun. 3, 1999. Jun. 28, 1999;99:37-38.

Uronis et al., Modulation of the intestinal microbiota alters colitis-associated colorectal cancer susceptibility. PLoS One. Jun. 24, 2009;4(6):e6026. doi: 10.1371/journal.pone.0006026.

Van Maren, Toll-like receptor signalling on Tregs: to suppress or not to suppress? Immunology. Aug. 2008;124(4):445-52. doi: 10.1111/j.1365-2567.2008.02871.x. Epub Jun. 28, 2008.

Van Scott et al., IL-10 reduces Th2 cytokine production and eosinophilia but augments airway reactivity in allergic mice. Am J Physiol Lung Cell Mol Physiol. Apr. 2000;278(4):L667-74.

Vann et al., The structure of the capsular polysaccharide (K5 antigen) of urinary-tract-infective Escherichia coli 010:K5:H4. A polymer similar to desulfo-heparin. Eur J Biochem. May 15, 1981;116(2):359-64.

Veldhoen et al., TGFbeta in the context of an inflammatory cytokine milieu supports de novo differentiation of IL-17-producing T cells. Immunity. Feb. 2006;24(2):179-89.

Velez et al., Type I Streptococcus pneumoniae carbohydrate utilizes a nitric oxide and MGC II-dependent pathway for antigen presentation. Immunol. 2008;127:73-82.

Verdu et al., Oral administration of antigens from intestinal flora anaerobic bacteria reduces the severity of experimental acute colitis in BALB/c mice. Clin Exp Immunol. Apr. 2000;120(1):46-50.

Videla et al., Role of intestinal microflora in chronic inflammation and ulceration of the rat colon. Gut. Aug. 1994;35(8):1090-7.

Vignali et al., How regulatory T cells work. Nat Rev Immunol. Jul. 2008;8(7):523-32. doi: 10.103 8/nri2343.

Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.

Viret et al., Molecular cloning and characterization of the genetic determinants that express the complete Shigella serotype D (Shigella sonnei) lipopolysaccharide in heterologous live attenuated vaccine strains. Mol Microbiol. Jan. 1993;7(2):239-52.

Wagner et al., Use of reporter cells to study endogenous retinoid sources in embryonic tissues. Methods Enzymol. 1997;282:98-107.

Wang et al., A bacterial carbohydrate links innate and adaptive responses through Toll-like receptor 2. J Exp Med. Dec. 25, 2006;203(13):2853-63. Epub Dec. 18, 2006.

Wang et al., Ozonolysis for selectively depolymerizing polysaccharides containing β-d-aldosidic linkages. Proc Natl Acad Sci U S A. Jun. 9, 1998; 95(12): 6584-6589.

Wang et al., Structural basis of the abscess-modulating polysaccharide A2 from Bacteroides fragilis. Proc Natl Acad Sci U S A. Dec. 5, 2000;97(25):13478-83.

Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.

Ward et al., The nucleotide sequence of the tnpA gene of Tn21, Nucleic Acids Research, vol. 15(4), 1987, 1799-1806.

Wehr et al., Anti-low-density lipoprotein antibodies in alcoholics without and with liver disease and in social drinkers. Alcohol Alcohol. Jan.-Feb. 1997;32(1):43-9.

Weinacht et al. Phase variation of the capsular polysaccharides of Bacteroides fragilis is dictated by site-specific recombinases. 2002 General Meeting of the American Society for Microbiology, May 19-23, 2002. Abstract.

Wen et al., Innate immunity and intestinal microbiota in the development of Type 1 diabetes. Nature. Oct. 23, 2008;455(7216):1109-13. doi: 10.1038/nature07336. Epub Sep. 21, 2008.

Wessels et al., Structural Determination and Immunochemical Characterization of the Type V Group B Streptococcus Capsular Polysaccharide, The Journal of Biological Chemistry, 266:6714-6719, 1991.

Wessels et al., Structure and immunochemistry of an oligosaccharide repeating unit of the capsular polysaccharide of type III group B Streptococcus. A revised structure for the type III group B streptococcal polysaccharide antigen. J Biol Chem. Jun. 15, 1987;262(17):8262-7.

Wexler, Bacteroides: the good, the bad, and the nitty-gritty. Clin Microbiol Rev. Oct. 2007;20(4):593-621.

Wiegandt et al., Carbohydrate Components of Extraneuronal Gangliosides from Bovine and Human Spleen, and Bovine Kidney, European Journal of Biochemistry, 15:287-292, 1970.

Willer et al., Twin concordance and sibling recurrence rates in multiple sclerosis. Proc Natl Acad Sci U S A. Oct. 28, 2003;100(22):12877-82. Epub Oct. 20, 2003.

Wirtz et al., Mouse models of inflammatory bowel disease. Adv Drug Deliv Rev. Sep. 30, 2007;59(11):1073-83. Epub Aug. 16, 2007.

Woessner et al., Long-term antibiotic treatment with roxithromycin in patients with multiple sclerosis. Infection. Dec. 2006;34(6):342-4.

Wong et al., Activation of peripheral Th17 lymphocytes in patients with asthma. Immunol Invest. 2009;38(7):652-64.

Woodruff et al., Sudden-onset severe acute asthma: clinical features and response to therapy. Acad Emerg Med. Jul. 1998;5(7):695-701.

Wu et al., Gut-residing segmented filamentous bacteria drive autoimmune arthritis via T helper 17 cells. Immunity. Jun. 25, 2010;32(6):815-27. doi: 10.1016/j.immuni.2010.06.001.

Wujek et al., A carbohydrate polymer that effectively prevents epidural fibrosis at laminectomy sites in the rat. Exp Neurol. Nov. 1991;114(2):237-45.

Xavier et al., Commensal flora: wolf in sheep's clothing. Gastroenterology. Apr. 2005;128(4):1122-6.

Xavier et al., Unravelling the pathogenesis of inflammatory bowel disease. Nature. Jul. 26, 2007;448(7152):427-34.

Xu J et al., A genomic view of the human-Bacteroides thetaiotaomicron symbiosis. Science. Mar. 28, 2003;299(5615):2074-6.

Yamazaki et al., CCR6 regulates the migration of inflammatory and regulatory T cells. J Immunol. Dec. 15, 2008;181(12):8391-401.

Yamazaki et al., Dendritic cells are specialized accessory cells along with TGF- for the differentiation of Foxp3+ CD4+ regulatory T cells from peripheral Foxp3 precursors. Blood. Dec. 15, 2007;110(13):4293-302. Epub Aug. 15, 2007.

(56) References Cited

OTHER PUBLICATIONS

Yokoyama et al., Adhesion behavior of rat lymphocytes to poly(ether)-poly(amino acid) block and graft copolymers. J Biomed Mater Res. Sep. 1986;20(7):867-78.

Yoshii, Cytotoxic effects of acrylates and methacrylates: relationships of monomer structures and cytotoxicity. J Biomed Mater Res. Dec. 15, 1997;37(4):517-24.

Young et al., In vitro and In vivo characterization of Helicobacter hepaticus cytolethal distending toxin mutants. Infect Immun. May 2004;72(5):2521-7.

Zabad et al., The clinical response to minocycline in multiple sclerosis is accompanied by beneficial immune changes: a pilot study. Mult Scler. May 2007; 13(4):517-26. Epub Feb. 9, 2007.

Zaleznik et al., A soluble suppressor T cell factor protects against experimental intraabdominal abscesses. J Clin Invest. Mar. 1985;75(3):1023-7.

Zaph et al., Commensal-dependent expression of IL-25 regulates the IL-23-IL-17 axis in the intestine. J Exp Med. Sep. 29, 2008;205(10):2191-8. doi: 10.1084/jem.20080720. Epub Sep. 1, 2008.

Zehnder et al., Extrarenal expression of 25-hydroxyvitamin d(3)-1 alpha-hydroxylase. J Clin Endocrinol Metab. Feb. 2001;86(2):888-94.

Zehnder et al., Expression of 25-hydroxyvitamin D3-1alpha-hydroxylase in the human kidney. J Am Soc Nephrol. Dec. 1999;10(12):2465-73.

Zhang et al., IL-10 is involved in the suppression of experimental autoimmune encephalomyelitis by CD25+CD4+ regulatory T cells. Int Immunol. Feb. 2004;16(2):249-56.

Zhao H et al. In vivo phase variation of MR/P fimbrial gene expression in Proteus mirabilis infecting the urinary tract. (1997) Mol Microbiol 23:1009-19.

Zhou et al., TGF-beta-induced Foxp3 inhibits T(H)17 cell differentiation by antagonizing RORgammat function. Nature. May 8, 2008;453(7192):236-40. doi: 10.1038/nature06878. Epub Mar. 26, 2008.

Zhu et al., Oral administration of type-II collagen peptide 250-270 suppresses specific cellular and humoral immune response in collagen-induced arthritis. Clin Immunol. Jan. 2007;122(1):75-84. Epub Oct. 11, 2006.

[No Author Listed] "Asthma" from the Centers for Disease Control and Prevention. Retrieved Nov. 13, 2012. www.cdc.gov/asthma/aag/2010/overview.html, pp. 1-2.

[No Author Listed] Drug Absorption, Bioavailability, and Routes of Administration. Goodman & Gilman's The Pharmacological Basis of Therapeutics, Tenth Edition, McGraw-Hill Medical Publishing Edition, New York, 2001, pp. 5-8.

[No Author Listed] National Public Health Partnership, The Language of Prevention. Melbourne: NPHP. 2006. 9 pages.

[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.

Adkins, T-cell function in newborn mice and humans. Immunol Today. Jul. 1999;20(7):330-5.

Adkins, Development of neonatal Th1/Th2 function. Int Rev Immunol. 2000;19(2-3):157-71.

Bell, Function of CD4 T cell subsets in vivo: expression of CD45R isoforms. Semin Immunol. Feb. 1992;4(1):43-50.

Bhaduri et al., Simple and rapid method for disruption of bacteria for protein studies. Appl Environ Microbiol. Oct. 1983;46(4):941-3.

Blander et al., Toll-dependent selection of microbial antigens for presentation by dendritic cells. Nature. Apr. 6, 2006;440(7085):808-12. Epub Feb. 19, 2006.

Bregenholt, Cells and Cytokines in the Pathogenesis of Inflammatory Bowel Disease: New Insights from Mouse T Cell Transfer Models. Exp Clin Immunogenet. Jun. 2000;17(3):115-129.

Brichford, Can You Prevent Multiple Sclerosis? Understanding factors that increase your risk of multiple sclerosis and what—if anything—you can do about them. EverydayHealth.com Dec. 2008; 2 pages.

Dadley-Moore, The sweet side of maturation. Nature Rev Immunol. Sep. 2005;5:674.

Deiβ, Treating multiple sclerosis with monoclonal antibodies: a 2013 update. Expert Rev Neurother. Mar. 2013;13(3):313-35. doi: 10.1586/ern.13.17.

Deslongchamps et al., Ozonolysis of Acetals. (1) Ester Synthesis, (2) THP Ether Cleavage, (3) Selective Oxidation of β-Glycoside, (4) Oxidative Removal of Benzylidene and Ethylidene Protecting Groups. Canadian J of Chem. 1971;49:2465-2467.

Deslongchamps et al., The Importance of Conformation in the Ozonolysis of Acetals. Canadian J Chem. 1972;50:3402-3404.

Deslongchamps et al., The Oxidation of Acetals by Ozone. Canadian J Chem. 1974;52:3651-3664.

Doig et al., The efficacy of the heat killing of *Mycobacterium tuberculosis*. J Clin Pathol. Oct. 2002;55(10):778-9.

Fontenot et al., Foxp3 programs the development and function of CD4+CD25+ regulatory T cells. Nat Immunol. Apr. 2003;4(4):330-6. Epub Mar. 3, 2003.

Gibson et al., Chapter 5: trans-Galactooligosaccharides as Prebiotics. Handbook of Functional Dairy Products. Edited by Colette Shortt and John O'Brien. Published by CRC Press. 2004. pp. 91-108.

Kirjavainen et al., Healthy gut microflora and allergy: factors influencing development of the microbiota. Ann Med. Aug. 1999;31(4):288-92.

Krause et al., An Inhibitor of Cell Proliferation Associated with Adhesion Formation Is Suppressed by N,O-Carboxymethyl Chitosan. J Invest Surg. 1988;11:105-113.

Ley et al., Evolution of mammals and their gut microbes. Science. Jun. 20, 2008;320(5883):1647-51. doi: 10.1126/science.1155725. Epub May 22, 2008.

Lindberg et al., Virulence factors in infections with bacteroides fragilis: isolation and characterization of capsular polysaccharide and lipopolysaccharide. Scand J Infect Dis Suppl. 1982;35:45-52.

MacPherson et al., IgA responses in the intestinal mucosa against pathogenic and non-pathogenic microorganisms. Microbes Infect. Oct. 2001;3(12):1021-35.

MacPherson et al., Interactions between commensal intestinal bacteria and the immune system. Nat Rev Immunol. Jun. 2004;4(6):478-85.

Mamessier et al., Cytokines in atopic diseases: revisiting the Th2 dogma. Eur J Dermatol. Mar.-Apr. 2006;16(2):103-13. Review.

Moorman et al., National Surveillance of Asthma: United States, 2001-2010. National Center for Health Statistics. Vital Health Stat. 2012;3(35) 67 pages.

Motta et al., T cells in asthma: Lessons from mouse models. Drug Discovery Today; Disease Models. 2006;3(3):199-204.

Ochoa-Reparaz, J. et al., The role of subcellular fractions of commensal Bacteroides fragilis in the control of experimental autoimmune encephalomyelitis. Multiple Sclerosis. 2009;15:S61. Poster P236.

Power et al., The human microbiome in multiple sclerosis: pathogenic or protective constituents? Can J Neurol Sci. Sep. 2010;37 Suppl 2:S24-33.

Raetz et al., Lipopolysaccharide endotoxins. Annu Rev Biochem. 2002;71:635-700. Epub Nov. 9, 2001.

Rose et al., Multifunctional role of dextran sulfate sodium for in vivo modeling of intestinal diseases. BMC Immunol. Aug. 1, 2012;13:41. doi: 10.1186/1471-2172-13-41.

Russell, Lethal effects of heat on bacterial physiology and structure. Sci Prog. 2003;86(Pt 1-2):115-37.

Tzeng et al., Translocation and surface expression of lipidated serogroup B capsular Polysaccharide in Neisseria meningitidis. Infect Immun. Mar. 2005;73(3):1491-505.

Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.

Whitfield, Biosynthesis and assembly of capsular polysaccharides in *Escherichia coli*. Annu Rev Biochem. 2006;75:39-68.

(56) References Cited

OTHER PUBLICATIONS

Zhang et al., Degradation of Wood Polysaccharide Model Compounds During Ozone Treatment. Journal of Pulp and Paper Science. Jan. 1997;23(1):J23-J27.

Mazmanian et al., Bacterial immunomodulatory regulation during mammalian health and disease. Harvard Medical School and Brigham and Women's Hospital. Presentation. Oct. 11, 2005. 51 pages.

Mazmanian et al., Host-bacterial symbiosis prevents intestinal inflammatory disease. California Institute of Technology. Presentation. Amgen. Jul. 2008. 47 pages.

Mazmanian et al., the evolution of symbiosis: from bacteria to commensal to beneficial microbe. Harvard Medical School and California Institute of Technology. Presentation. Oct. 4, 2006. 24 pages.

International Search Report and Written Opinion for Application No. PCT/US2014/037192 mailed Sep. 19, 2014.

International Preliminary Report on Patentability for Application No. PCT/US2014/037392 mailed Nov. 19, 2015.

Becker et al., TGF-beta suppresses tumor progression in colon cancer by inhibition of IL-6 trans-signaling. Immunity. Oct. 2004;21(4):491-501.

[No Author Listed] MS the Disease. National Multiple Sclerosis Society. http://www.nationalmssociety.org/, 2014. 4 pages.

Blumberg et al, Microbiota, disease, and back to health: a metastable journey. Sci Transl Med. Jun. 6, 2012;4(137):137rv7. doi: 10.1126/scitranslmed.3004184.

Bollrath et al., gpl 30-mediated Stat3 activation in enterocytes regulates cell survival and cell-cycle progression during colitis-associated tumorigenesis. Cancer Cell. Feb. 3, 2009; 15(2):91-102. doi: 110.1016/j.ccr.2009.01.002.

Clemente et al., Infliximab modifies mesenteric adipose tissue alterations and intestinal inflammation in rats with TNBS-induced colitis. Scand J Gastroenterol. Sep. 2012:47(8-9):943-50. doi: 10.3109/00365521.2012.688213. Epub May 28, 2012.

Coussens et al., Inflammation and cancer. Nature. Dec. 19-26, 2002;420(6917):860-7.

Garrett et at, Colitis-associated colorectal cancer driven by T-bet deficiency in dendritic cells. Cancer Cell. Sep. 8, 2009;116(3):208-19. doi: 10.1016/j.ccr.2009.07.015.

Garrett et al., Enterobacteriaceae act in concert with the gut microbiota to induce spontaneous and maternally transmitted colitis. Cell Host Microbe. Sep. 16, 2010;8(3):292-300. doi: 10.11016/j.chom.2010.08.004.

Grivennikov et al., IL-6 and Stat3 are required for survival of intestinal epithelial cells and development of colitis-associated cancer. Cancer Cell. Feb. 3, 2009;15(2):103-13. doi: 10.1016/j.ccr.2009.01.001.

Hu et al., Inflammation-induced tumorigenesis in the colon is regulated by caspase-1 and NLRC4. Proc Natl Acad Sci U S A. Dec. 14, 2010;107(50):21635-40. doi: 10.1073/pnas.1016814108. Epub Nov. 30, 2010.

Itzkowitz et al., Diagnosis and management of dysplasia in patients with inflammatory bowel diseases. Gastroenterology. May 2004;126(6):1634-48.

Jawad et al., Inflammatory bowel disease and colon cancer. Recent Results Cancer Res. 2011;185:99-115. doi: 10.1007/978-3-642-03503-6_6.

Kuper et al., Infections as a major preventable cause of human cancer. J Intern Med. Sep. 2000;248(3):171-83.

Lee et al., Bacterial colonization factors control specificity and stability of the gut microbiota. Nature. Sep. 19, 2013;501(7467):426-9. doi: 10.1038/nature12447. Epub Aug. 18, 2013.

Mantovani et al., Cancer-related inflammation. Nature. Jul. 24, 2008;454(7203):436-44. doi: 10.1038/nature07205.

Popivanova et al., Blocking TNF-alpha in mice reduces colorectal carcinogenesis associated with chronic colitis. J Clin Invest. Feb. 2008;118(2):560-70. doi: 10.1172/JCI32453.

Tong et al., Mouse models of colorectal cancer. Chin J Cancer. Jul. 2011;30(7):450-62. doi: 10.5732/cjc.011.10041.

Triantafillidis et al., Colorectal cancer and inflammatory bowel disease: epidemiology, risk factors, mechanisms of carcinogenesis and prevention strategies. Anticancer Res. Jul. 2009;29(7):2727-37.

Xie et al., Cancer in inflammatory bowel disease. World J Gastroenterol. Jan. 21, 2008;14(3):378-89.

* cited by examiner

US 9,539,281 B2

LIPID-CONTAINING PSA COMPOSITIONS, METHODS OF ISOLATION AND METHODS OF USE THEREOF

RELATED APPLICATIONS

This application is a national stage filing under 35 U.S.C. §371 of International Application No. PCT/US2012/046384 filed Jul. 12, 2012, which was published under PCT Article 21(2) in English, and which claims the benefit of U.S. Provisional Application Ser. No. 61/507,074, filed on Jul. 12, 2011, both entitled "LIPID-CONTAINING PSA COMPOSITIONS, METHODS OF ISOLATION AND METHODS OF USE THEREOF", the entire contents of each of which are incorporated by reference herein.

FIELD OF THE INVENTION

The invention relates to compositions of capsular polysaccharide A (PSA) isolated from *B. fragilis*, and methods of isolation and purification and/or use thereof.

BACKGROUND OF THE INVENTION

Capsular polysaccharide A (PSA) of *Bacteroides fragilis* (*B. fragilis*) NCTC9343 has been reported to be an immunomodulator with therapeutic and preventative applications. U.S. Pat. Nos. 5,679,654 and 5,700,787; Tzianabos A O et al. (2000) J Biol Chem 275:6733-40.

SUMMARY OF THE INVENTION

Polysaccharide A (PSA), a polysaccharide of the bacterium Bacterioides fragilis (*B. fragilis*), has potent anti-inflammatory capacity mediated, at least in part, by its ability to activate CD4+ T regulatory cells to produce the cytokine IL-10.

The invention is based on the discovery of a significantly more potent form of PSA, made by *B. fragilis*, that comprises a lipid. This lipid is likely used by the microbe to anchor PSA in its outer membrane. Extraction techniques used heretofore do not yield this lipid-conjugated PSA. The lipid typically comprises less than 2% (w/w) of the native PSA-LT molecule. Proton NMR analysis of PSA does not distinguish the lipidated and non-lipidated forms. Rather, it has been found in accordance with the invention that presence of the lipidated from can only be visualized using specific gel staining techniques.

In accordance with the invention, it has been shown that the lipid may be removed from PSA-LT using mild hydrolysis (e.g., with dilute acetic acid) and subsequent extraction with an organic solvent (e.g., chloroform). This hydrolyzed form of PSA has an activity that is markedly reduced compared to the lipidated form of PSA (i.e., PSA-LT), and that its activity is at a level comparable to the earlier described PSA (i.e., the non-lipidated form of PSA). Accordingly, the invention provides, inter alia, a more potent form of PSA (i.e., PSA-LT) having enhanced IL-10 inducing activity and Treg maturation activity. It has also been found, in accordance with the invention, that PSA-LT is significantly more protective and therapeutic in animal models of inflammatory conditions such as but not limited to multiple sclerosis (i.e., the EAE animal model) and inflammatory bowel disease than the originally described non-lipidated form of PSA.

The invention therefore provides, inter alia, compositions comprising the lipidated form of PSA, methods for its isolation and purification, and in vitro and in vivo methods of use thereof.

Thus, in one aspect, the invention provides a method comprising extracting, into an aqueous phase, a capsular complex from *B. fragilis* using a mixture of phenol and water at high temperature, precipitating polysaccharide A (PSA) from the aqueous phase using ethanol, acid-treating the precipitate using 2% acetic acid at high temperature, wherein the method is performed at a pH equal to or less than about 9. In some embodiments, the pH ranges from about 4 to about 9, or from about 4 to less than about 9.

In another aspect, the invention provides a method comprising extracting, into an aqueous phase, a capsular complex from *B. fragilis* using a mixture of phenol and water at high temperature, precipitating polysaccharide A (PSA) from the aqueous phase using ethanol, acid-treating the precipitate using 2% acetic acid at high temperature, wherein the method is performed in the absence of sodium deoxycholate.

In some embodiments, each method may further comprise, after acid-treatment, a step of purifying PSA by size exclusion in a detergent-free buffer. In some embodiments, each method may further comprise dialysis of size excluded PSA.

In some embodiments, extraction occurs at 60-75° C. In some embodiments, extraction occurs at about 68° C.

In some embodiments, acid-treatment occurs at about 90° C. for about 3 hours.

In some embodiments, each method is performed in the absence of sodium deoxycholate. In some embodiments, each method is performed in the absence of detergent.

In some embodiments, *B. fragilis* is a PSA-overexpressing strain of *B. fragilis* such as but not limited to strain 9343.

In another aspect, the invention provides a composition comprising isolated lipid-containing polysaccharide A (PSA-LT) produced by any of the foregoing methods. The isolated lipid-conjugated polysaccharide A comprises one or more non-LPS lipids. In some embodiments, the composition is formulated for oral administration to a subject.

In another aspect, the invention provides a composition comprising isolated *B. fragilis* non-LPS lipid-conjugated polysaccharide A (PSA). The non-LPS lipid may be covalently conjugated to PSA. In some embodiments, the isolated *B. fragilis* non-LPS lipid-conjugated PSA comprises less than 1%, less than 0.5%, less than 0.1%, less than 0.05%, or less than 0.01% (w/w) of non-LPS lipid conjugated to PSA. In some embodiments, the isolated *B. fragilis* non-LPS lipid-conjugated PSA comprises non-LPS lipid in the range of about 0.1% to 2% (w/w) or about 0.1% to 1% (w/w), including about 0.5% (w/w). The isolated lipid-conjugated polysaccharide A comprises one or more non-LPS lipids. In some embodiments, the composition is formulated for oral administration to a subject.

In another aspect, the invention provides a composition comprising isolated *B. fragilis* lipid-conjugated polysaccharide A (PSA) and less than or about 0.5% (w/w) LPS, wherein the composition comprising the isolated *B. fragilis* lipid-conjugated polysaccharide A, when treated with 2% acetic acid and run on a 16.5% Tris-Tricine SDS-PAGE gel and reverse-stained using zinc sulphate and imidazole, demonstrates a band at above 60 kD (PSA-LT) and a band at about 5 kD. The isolated *B. fragilis* lipid-conjugated polysaccharide A comprises one or more non-LPS lipids. The lipid(s) may be covalently conjugated to the carbohydrate portion of PSA-LT. Under some circumstances, the bond between the lipid(s) and the carbohydrate portion of PSA-LT is not susceptible to cleavage by snake venom phosphodiesterase. In some embodiments, the composition demonstrates LPS bands at 6 and 8 kD of less intensity than the band at about 5 kD. In some embodiments, the composition is formulated for oral administration to a subject.

In another aspect, the invention provides a composition comprising isolated B. fragilis lipid-conjugated polysaccharide A wherein the composition comprises about 99% PSA, about 0.5% non-LPS lipid, and about 0.5% LPS.

In another aspect, the invention provides a composition comprising isolated B. fragilis lipid-conjugated polysaccharide A wherein the composition comprises about 97%-99% PSA, about 0.5%-2% non-LPS lipid, and about 0.5% LPS.

In another aspect, the invention provides a composition comprising isolated PSA-LT wherein the isolated PSA-LT comprises about 99.5% (w/w) of the composition and LPS represents about 0.5% (w/w) of the composition.

In various embodiments of the foregoing aspects, the compositions are essentially free of nucleic acids, proteins and/or other bacterial contaminants.

In another aspect, the invention provides a method comprising administering to a subject having a condition associated with inflammation an effective amount of any of the foregoing PSA-LT-comprising compositions. In another aspect, the invention provides a method comprising administering to a subject at risk of a recurrence of a condition associated with inflammation an effective amount of any of the foregoing PSA-LT-comprising compositions.

In some embodiments, the method is a method of reducing the likelihood of a recurrence of the condition or reducing the frequency of future recurrences. In some embodiments, the method is a method of reducing the severity of symptoms associated with the condition, whether such symptoms are present in the first manifestation, in a recurrence, or chronically.

In some embodiments, the condition is an autoimmune disease. The autoimmune disease may be multiple sclerosis, Crohn's disease, ulcerative colitis, rheumatoid arthritis, or type I diabetes.

In some embodiments, the condition is asthma. In some embodiments, the condition is obesity.

In some embodiments, the composition may be administered to the subject by inhalation (e.g. nebulization), by oral administration, or by injection. In some embodiments, the composition is orally administered to the subject.

In another aspect, the invention provides a method comprising administering to a subject at risk of developing a post-surgical adhesion an effective amount of any of the foregoing PSA-LT comprising compositions. In some embodiments, the PSA-LT comprising composition is administered prior to surgery, during surgery, after surgery, or any combination thereof including but not limited to prior to and during surgery.

In another aspect, the invention provides a method comprising administering to a subject having or at risk of developing an abscess an effective amount of any of the foregoing PSA-LT comprising compositions. In some embodiments, the subject is also administered an antibacterial agent such as an antibiotic. In some embodiments, the PSA-LT comprising composition is administered prior to development of an abscess and/or prior to the manifestation of symptoms associated with an abscess. In some embodiments, the PSA-LT comprising composition is administered after an abscess has been detected or diagnosed and/or after symptoms associated with an abscess are manifested.

In still another aspect, the invention provides a method comprising analyzing a composition suspected of comprising PSA-LT using a Tris-Tricine SDS-PAGE gel that is reversed stained with zinc sulphate and imidazole. In some embodiments, the gel is a 16.5% Tris-Tricine SDS-PAGE gel. In some embodiments, the composition is a bacterial fraction, such as a B. fragilis fraction. In some embodiments, the bacterial fraction has been subjected to a hot phenol/water extraction, an ethanol precipitation, a mild acid-treatment (e.g., at an acidic pH at or above 4, typically in the range of 4-5), and/or size exclusion. In some embodiments, the composition, including the bacterial fraction, has not been contacted with sodium deoxycholate. In some embodiments, the composition, including the bacterial fraction, has not been contacted with a detergent. In some embodiments, the method is a method of detecting presence of a non-LPS lipid in the composition. In some embodiments, the method is a method of detecting PSA-LT in the composition. The presence of PSA, LPS and/or non-LPS lipid may be detected using the method. The amount of PSA, LPS and/or non-LPS lipid may be measured using the method.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

DETAILED DESCRIPTION OF THE INVENTION

Figure 1:
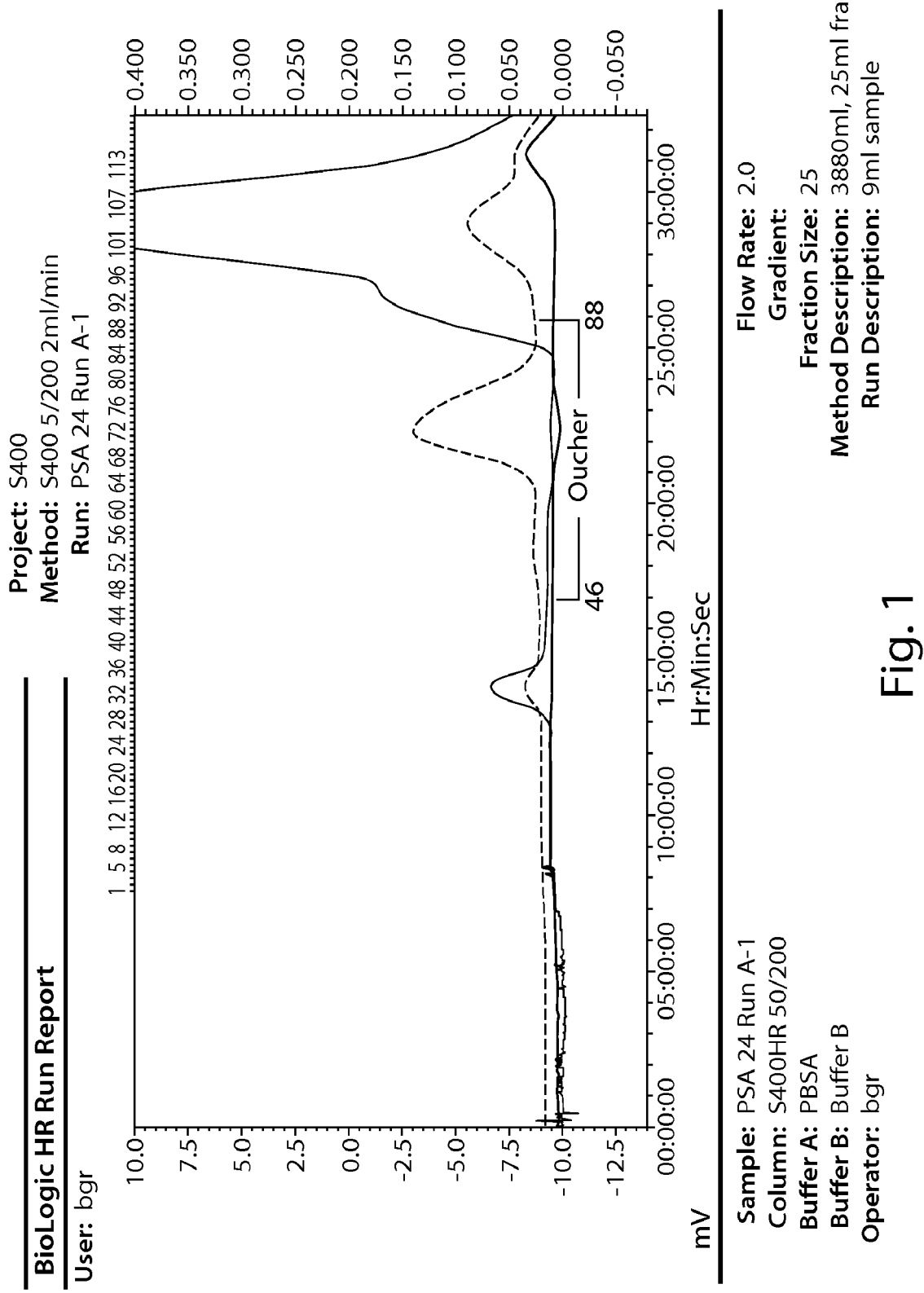
FIG. 1 is an elution profile of an S400 column.

The invention is premised on the surprising and unexpected discovery of a lipidated form of polysaccharide A (PSA), referred to herein as PSA-LT, from B. fragilis. It has been found, according to the invention, that the prior art methods for isolating and purifying PSA from B. fragilis inadvertently and unknowingly removed a lipid component that is conjugated to native PSA. The native, lipidated form of PSA is more potent than the non-lipidated form that has been previously isolated and purified, as demonstrated by both in vitro and in vivo assays. As demonstated in the Examples, the lipidated form of PSA is better able to induce IL-10 production (and therefore better able to interact with Treg cells) and better able to prevent an experimentally induced murine form of multiple sclerosis (i.e., experimental autoimmune encephalitis, EAE).

Accordingly, the invention provides compositions comprising the isolated lipidated form of PSA (PSA-LT), methods of isolating and purifying PSA-LT from B. fragilis, and methods of using isolated PSA-LT in vitro and in vivo. The invention contemplates that the isolated PSA-LT may be completely (or fully) lipidated or it may be partially lipidated. The degree of lipidation will depend upon the isolation methods, including for example the degree of acid hydrolysis. It is also to be understood that the compositions of the invention typically comprise a plurality of PSA-LT molecules, and that the plurality may exhibit variation in the degree of lipidation. Accordingly, in some instances the characteristics provided herein relate to the composition comprising a plurality of PSA-LT rather than a single PSA-LT molecule.

Structure of PSA and PSA-LT

The invention relates in part to a newly discovered lipidated form of PSA from B. fragilis. The lipidated form is referred to as PSA-LT. This lipidated form is comprised of a polysaccharide and one or more lipid chains (or tails). The carbohydrate portion of the newly discovered molecule is referred to as PSA. This is also the form of the polysaccharide that has been previously isolated and analyzed. It was not known prior to the invention that this polysaccharide existed in nature in a lipid-conjugated form.

Polysaccharide A (PSA) comprises a tetrasaccharide repeating unit that is –3) α-D-AAT Galp-(1→4)-[β-D-Galf-(1→3) α-D-GalpNAc-(1→3)-[4,6-pyruvate]-β-D-Galp-(1→. It possesses zwitterionic behavior as conferred by a positive charge on its free amine group and a negative charge on its free carboxyl group (per repeating tetrasaccharide unit). Its naturally occurring state is composed of over 60 tetrasaccharide repeating units (e.g., up to and including in some instances about 100, or about 200, or about 300 repeated units on average), and it has an average molecular size of about 150 kD (with a range of about 60 kD to 2000 kD).

The repeating tetrasaccharide unit of PSA has a structure as follows:

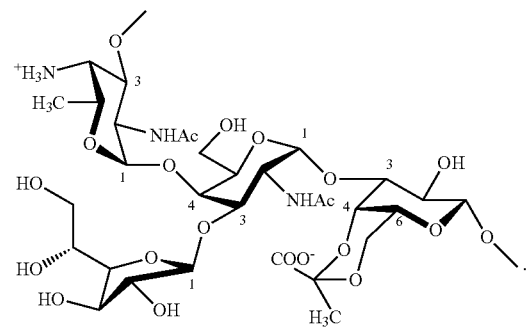

The invention is based in part on the isolation of a lipidated form of PSA from B. fragilis using isolation and purification methods that maintain the lipid conjugated to the PSA. The lipidated form of PSA, referred to herein as PSA-LT, comprises tetrasaccharide repeating unit structure of PSA covalently conjugated to one or more lipid chains (or tails or moieties, as used interchangeably herein). The bond between the lipid and PSA is not susceptible to cleavage using phosphodiesterases extracted from snake venom. The lipid moieties may be conjugated to PSA via ester or amide linkages. There may be one or more lipid chains (or tails) per PSA molecule.

The invention further provides compositions comprising isolated PSA-LT. As used herein, with respect to PSA-LT, the term "isolated" intends that the PSA-LT is physically separated from its natural environment (i.e., a B. fragilis cell). Compositions comprising isolated PSA-LT may comprise other components including LPS and/or non-lipidated PSA. In some embodiments, the amount of LPS present in such compositions is about 0.5% (w/w) or less.

In some embodiments, the compositions of the invention comprise about 99% PSA, 0.5% non-LPS lipid, and about 0.5% LPS. It will be understood that in some instances the compositions comprise PSA conjugated to its lipid(s) (i.e., PSA-LT), even though characterization of such compositions may require cleavage of the lipid from PSA (e.g., in the gel systems described herein). As will be understood in the art, LPS refers to lipopolysaccharide. As used herein, a non-LPS lipid is a lipid that is not LPS. The amounts of PSA, LPS and non-LPS lipid can be determined using a gel system such as that described herein. In some embodiments, the compositions are essentially free of contaminants such as nucleic acids such as DNA and RNA and proteins. Essentially free, as used herein, intends that these contaminants represent about or less than 0.1% (w/w) of the composition. In some instances, such contaminants may be undetectable.

The invention provides compositions for use in vitro and in vivo. In vitro, the compositions may be used as analytical tools or assay standards. In vivo, the compositions may be used or in experimental models, such as animal models, of human disease or in humans or other subjects in need of immune regulation. When used in vivo, the compositions are pharmaceutically acceptable, intending that they are suitable for administration into a subject. They may or may not be used prophylactically or therapeutically in such subjects.

PSA-LT Isolation Methods

The method provides general and specific methods for isolating and purifying PSA-LT from *B. fragilis*. It is to be understood that these methods may be performed on any strain of *B. fragilis* provided it produces PSA. Such strains include naturally occurring strains or mutant strains such as the overexpressing strain 9343.

It has been found that the prior art methods used to isolate and purify PSA removed the lipid tail from the polysaccharide. The invention provides methods that spare the lipid tail, and thereby yield a lipidated form of PSA that is functionally more potent than its previously isolated non-lipidated form. The isolation methods of the invention differ from the prior art isolation methods in a number of ways. First, the instant methods perform hydrolysis with mild acid (e.g., at a pH of about 4, or in the range of 4-5) at an early step in the purification process rather than a later step as was done in the prior art. Second, the instant methods perform molecular sieve chromatography in a neutral buffer solution (Tris) in the absence of sodium deoxycholate (DOC) which was used in the prior art methods. Third, the pH throughout the isolation is 9 or less (e.g., about 4 to about 9 or less), and in most steps is maintained in a neutral range.

Briefly, isolation and purification of PSA-LT comprises (1) growth of *B. fragilis* (wild type or mutant strain that produces PSA, including strains that overexpress PSA) under anaerobic conditions, (2) isolation of the capsular complex from *B. fragilis*, and (3) ethanol precipitation of PSA-LT, (4) mild acid-treatment. The capsular complex may be isolated using for example a hot phenol/water extraction. Ethanol precipitation of PSA-LT may be preceded by treatment with DNase, RNase and/or pronase. The acid-treatment may be performed using dilute acid (e.g., 2% acetic acid) at elevated temperature. The elevated temperature may range from 80-100° C., 85-95° C., and in some instances is about 90° C. The treatment may last for 1 hour, 2 hours, 3 hours or longer. In some instances, the acid treatment is performed using 2% acetic acid at 90° C. for 3 hours.

PSA-LT may be further purified from the precipitate by size exclusion. For example, the precipitate may be dissolved in a neutral buffer such as but not limited to PBS, and then applied on a S-400 size exclusion column. This size exclusion step is performed in the absence of sodium deoxycholate, and in some instances in the absence of any detergent. PSA-LT containing fractions are then pooled, optionally analyzed, and dialyzed. The final dialysate may be lyophilized.

Purity may be assessed by nuclear NMR and/or SDS PAGE gel as described in greater detail herein.

Analysis and Characterization of PSA-LT and Comparison to PSA

A. Structural Characterization of PSA-LT

FIG. 1 shows an elution profile of an S400 column in Tris buffered saline monitored by absorption at 280 nm. As stated above, fractions were tested by double diffusion in agar with an antibody to PSA-LT.

Figure 2:
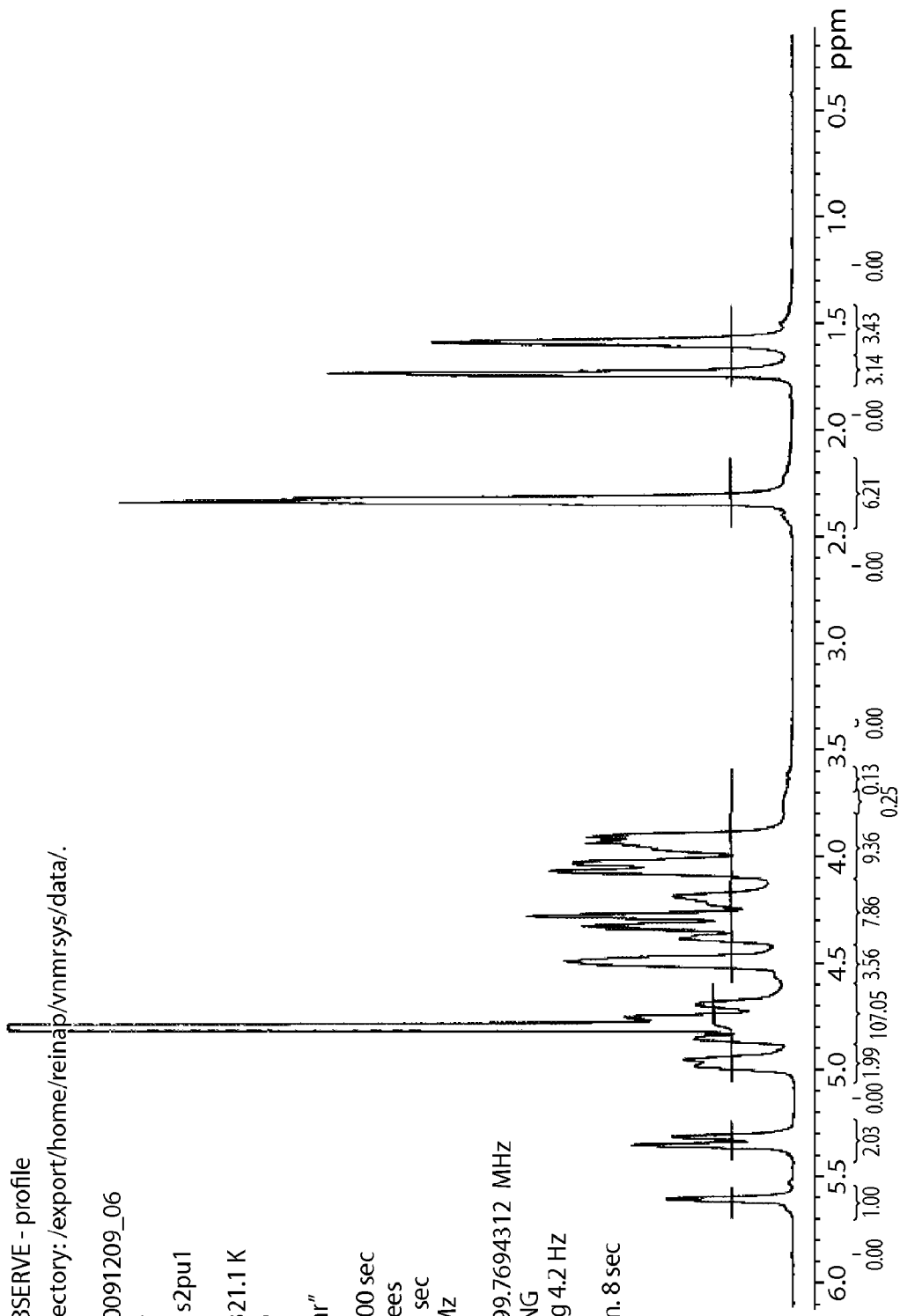
FIG. 2 is a proton nuclear magnetic resonance spectroscopy profile of purified PSA-LT.

FIG. 2 is a proton nuclear magnetic resonance spectroscopy profile of purified PSA-LT done on a 600 mHz NMR. The carbohydrate structure of this molecule precisely fits the published spectrum for PSA. This indicates that the carbohydrate portion of PSA-LT is identical to PSA. The very small percentage (m/m) of PSA-LT that is attributable to lipid is not observed by this high-resolution technique.

Figure 5:
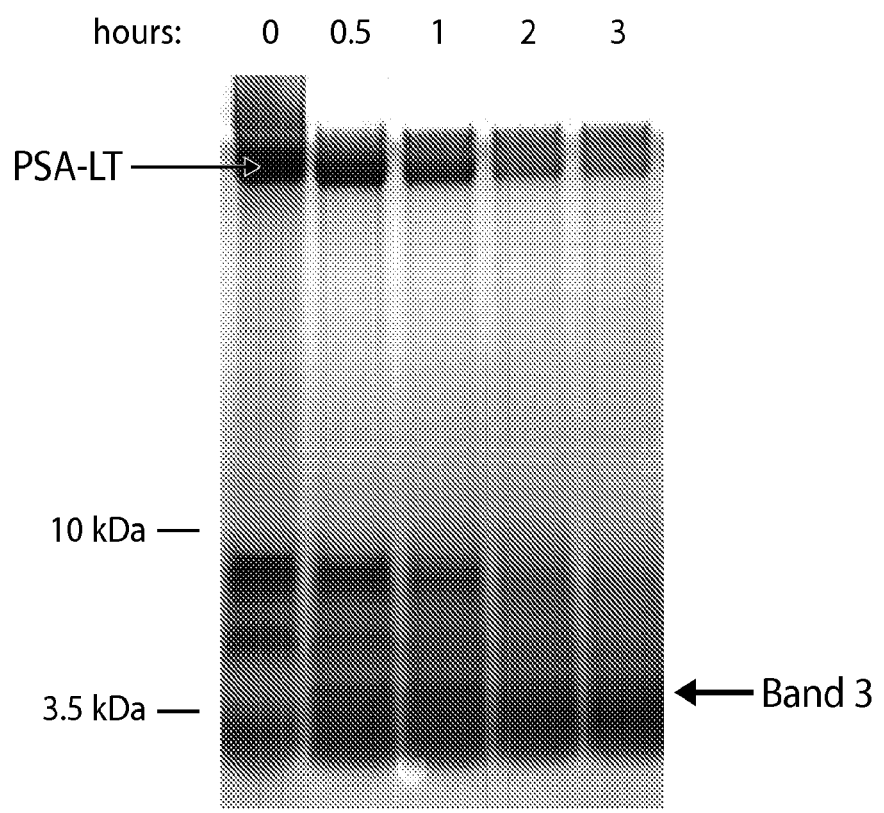
FIG. 5 is a photograph of a gel showing the results of an acid treatment time course of PSA-LT containing composition.

FIG. 5 shows the results of an acid treatment time course of PSA-LT using a 16.5% Tris-Tricine SDS-PAGE gel reverse stained with zinc sulphate/imidazole staining. This staining protocol allows one to observe both the carbohydrate (i.e., PSA) and lipid portions of PSA-LT in the same gel system. Four mg of a 5 mg/ml PSA-LT (Lot 26) was treated with 2% acetic acid at 90° C. for various periods of time followed by neutralization with NaOH and dialysis. One hundred micrograms of the resultant product was run on a 16.5% Tris-Tricine SDS-PAGE gel and reverse-stained as described above. The Figure clearly shows the disappearance of the LPS bands (at about 6 and 8 kD) and the emergence of a lipid band (labeled Band 3) at about 5 kD with increasing hydrolysis time.

Figure 6:
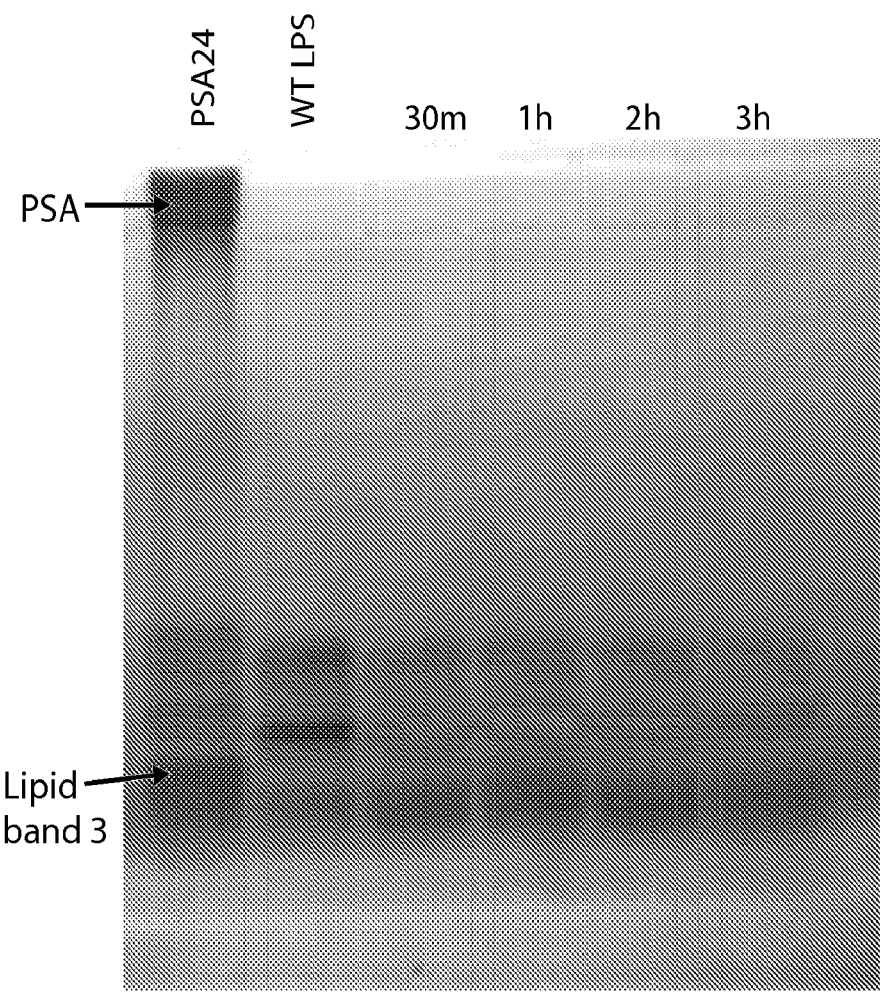
FIG. 6 is a photograph of a gel showing the effect of acid treatment on B. fragilis LPS compared to lipidated-PSA (PSA24).

To determine whether Band 3 emanated as a hydrolytic product of PSA-LT (very top of the gel) or LPS (Bands at approximately 8 kDa and 6 kDa), we took purified *B. fragilis* LPS and hydrolyzed under identical conditions to which we had hydrolyzed PSA-LT. Importantly, no Band 3 appeared after hydrolysis of LPS, but was distinctly present after hydrolysis of PSA-LT (Lot 24). (FIG. 6)

Figure 13:
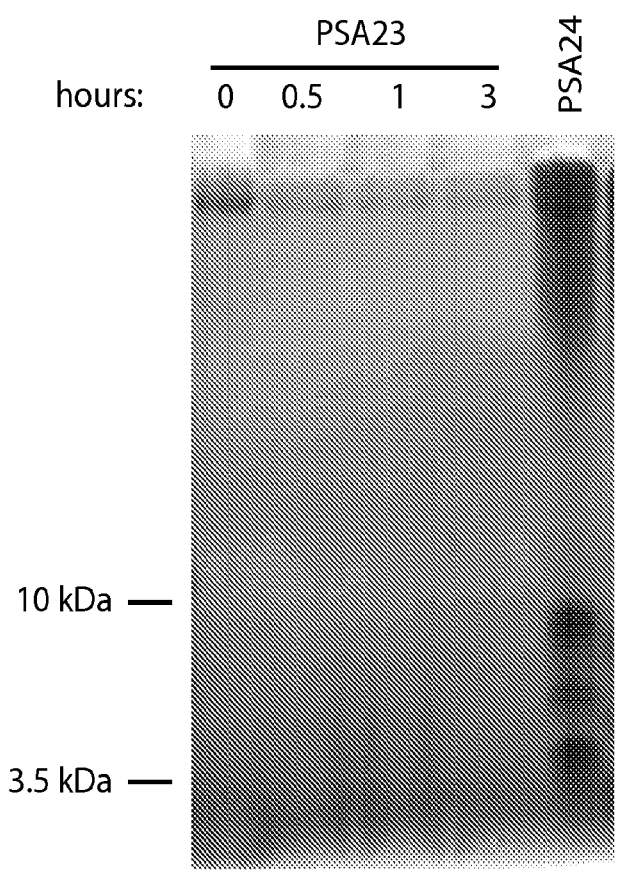
FIG. 13 is a photograph of a gel showing the results of an acid treatment time course of a PSA-containing composition (PSA23) produced using a prior art isolation method and a PSA-LT containing composition (PSA24). Notably, there is no Band 3 following acid treatment of PSA23.

In addition, no Band 3 has been observed in PSA-containing compositions prepared using prior art isolation methods, such as for example Lot 23 (PSA23, FIG. 13). The Figure shows the results of an acid treatment on 1 mg of 1.3 mg/ml PSA23 in water (2% acetic acid at 90° C. and neutralized with NaOH). 100 ug of the treated fraction was run on a 16.5% Tris-Tricine SDS-PAGE gel and reverse-stained with zinc sulphate/imidazole. A PSA24 preparation comprising PSA-LT was run alongside as a comparator.

Figure 7:
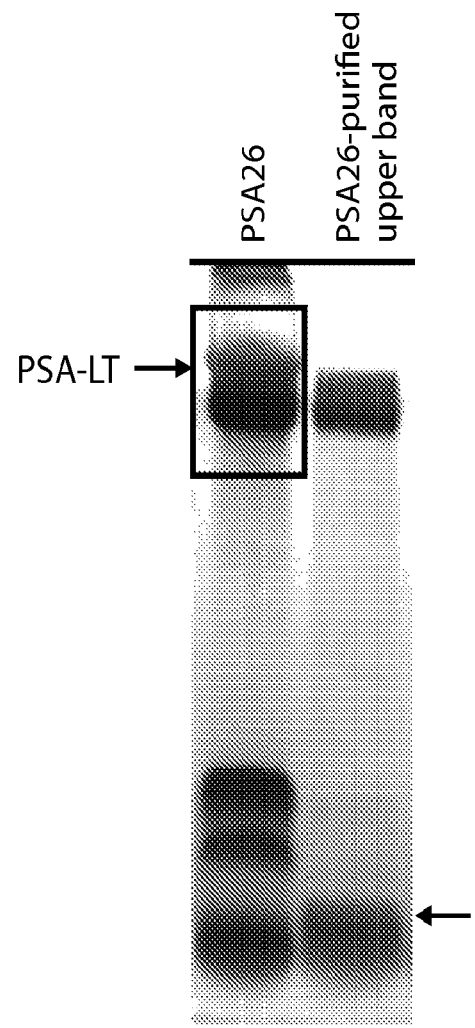
FIG. 7 is a photograph of a gel showing the presence of lipid (arrow) in the PSA-LT preparation (PSA26). The higher molecular weight PSA (shown in the box) was cut out from and eluted from the gel using 5% triethylamine. The gel-extracted PSA shows the lipid band (labeled with the arrow).

To confirm that Band 3 was a hydrolytic product of PSA-LT, the large molecular weight PSA-LT, as observed in the gel on the left in FIG. 7, was further analyzed. The box indicates the band cut out of the gel for further analysis. The product eluted from the gel was then hydrolyzed and studied again by running it in the same gel system, as seen in the right hand column of FIG. 7. Band 3 can be observed, as indicated by the arrow, after hydrolysis of the large molecular weight PSA-LT.

B. Functional Characterization of PSA-LT

Experiments were then performed to determine if the immunologic activity of the PSA-LT preparation was affected by the step in the prior purification process where hydrolysis likely takes place. PSA-LT (Lot 24) was hydrolyzed very early in the purification process at a time immediately after separation of the aqueous phase from the initial phenol/water extraction step.

PSA-LT was tested for its ability to induce IL-10 production in a splenic dendritic cell and T cell co-culture. This assay was performed as follows: (1) splenic DCs are isolated using mouse anti-CD11c microbeads (Miltenyi Biotec cat#130-052-001); (2) CD4$^+$ T cells are isolated using Mouse T cell CD4 Subset Column Kit (R&D systems cat#MCD4C-1000); (3) $2 \times 10^4$ CD11c$^+$ DCs and $10^5$ CD4$^+$ T cells are mixed and 1 µg/ml anti-CD3 (BD Pharmingen cat#553057) is added; (4) the culture is then stimulated with 100 µg/ml PSA and the cells are incubated for 5 days; and (5) supernatants are harvested and analyzed by ELISA for the presence of IL-10.

Figure 3:
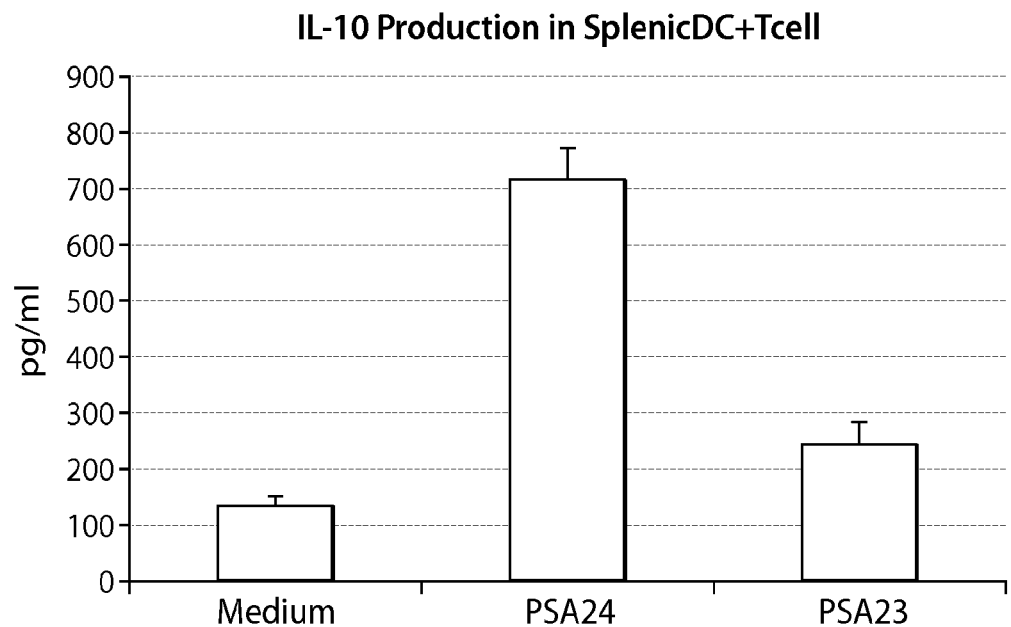
FIG. 3 is a histogram of IL-10 production in a splenic dendritic cell (DC) T cell co-culture system using lipidated (PSA24) and non-lipidated (PSA23) forms of PSA.

FIG. 3 demonstrates that, in terms of IL-10 production in this co-culture system, PSA-LT (shown as PSA24) is approximately 3 fold more potent than PSA made by the prior art method (shown as PSA 23).

Figure 4:
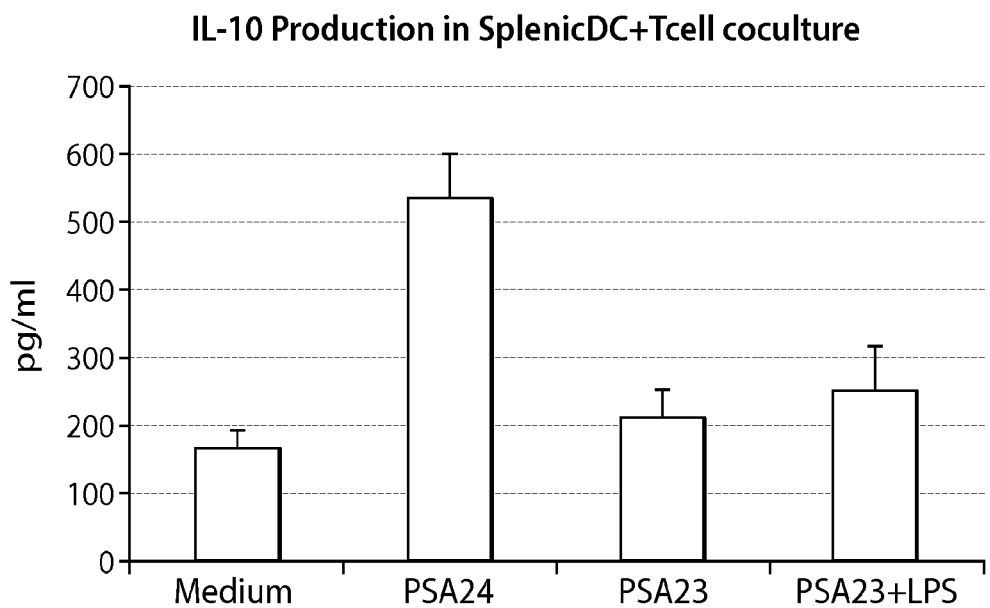
FIG. 4 is a histogram of IL-10 production in a splenic dendritic cell (DC) T cell co-culture system using lipidated (PSA24) and non-lipidated (PSA23) forms of PSA, and non-lipidated (PSA23) form of PSA with added LPS (PSA23+LPS).

Because PSA24 had small amounts of contaminating LPS (approximately 0.5%, w/w) we added purified *B. fragilis* LPS to PSA Lot 23 (PSA23) and determined that the addition of LPS to a PSA lot containing no LPS did not enhance (and thus did not reconstitute) its ability to induce IL-10 in the co-culture system. (FIG. 4)

Figure 8:
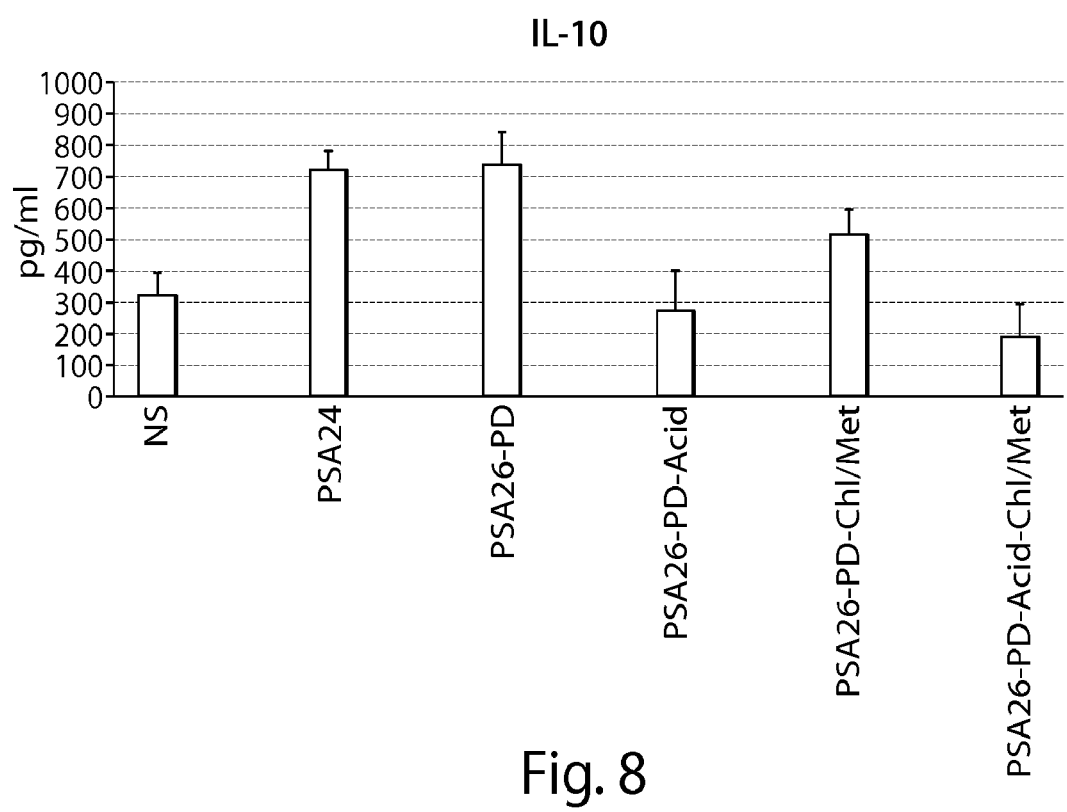
FIG. 8 is a histogram showing IL-10 production as a function of PSA-LT preparation protocol, acid hydrolysis and/or organic solvent dissolution.

As shown in FIG. 8, PSA-LT 24 was quite active in inducing IL-10 production in the DC T cell co-culture system. PSA-LT (Lot 26, and shown as PSA26-PD in this Figure) was similarly active prior to any hydrolysis step. Following further purification of unhydrolyzed PSA-LT (Lot 26) by 5400 chromatography, this material was hydrolyzed under the same conditions as the earlier phase hydrolysis of PSA-LT (Lot 24). In contrast to PSA-LT hydrolyzed early in the purification process, the PSA-LT hydrolyzed later in the process had lost much of its capacity to induce IL-10 in the co-culture system. If unhydrolyzed PSA-LT (Lot 26) was extracted directly with chloroform there was no statistically significant loss of IL-10 inducing capacity. Finally, if later stage PSA-LT (Lot 26) was hydrolyzed and chloroform extracted, all residual IL-10 inducing capacity was lost. Therefore, the lipid fraction of PSA-LT is significantly removed by hydrolysis but not by organic solvents.

However, following hydrolysis the material is soluble in an organic solvent indicating that there is a hydrolysable covalent bond between PSA and a lipid. The fact that chloroform extraction directly on PSA-LT did not remove IL-10 inducing capacity unless PSA-LT was first hydrolyzed indicates that the lipid component is covalently attached. The fact that the lipid is not seen on NMR, combined with the finding of Band 3 after hydrolysis of PSA-LT indicates that the lipid is an extremely small percent of the overall mass of PSA-LT and most likely represents the covalently linked lipids at the reducing terminus of the polysaccharide. Such lipids may be used by Gram negative bacteria for membrane insertion of a polysaccharide.

Figure 9:
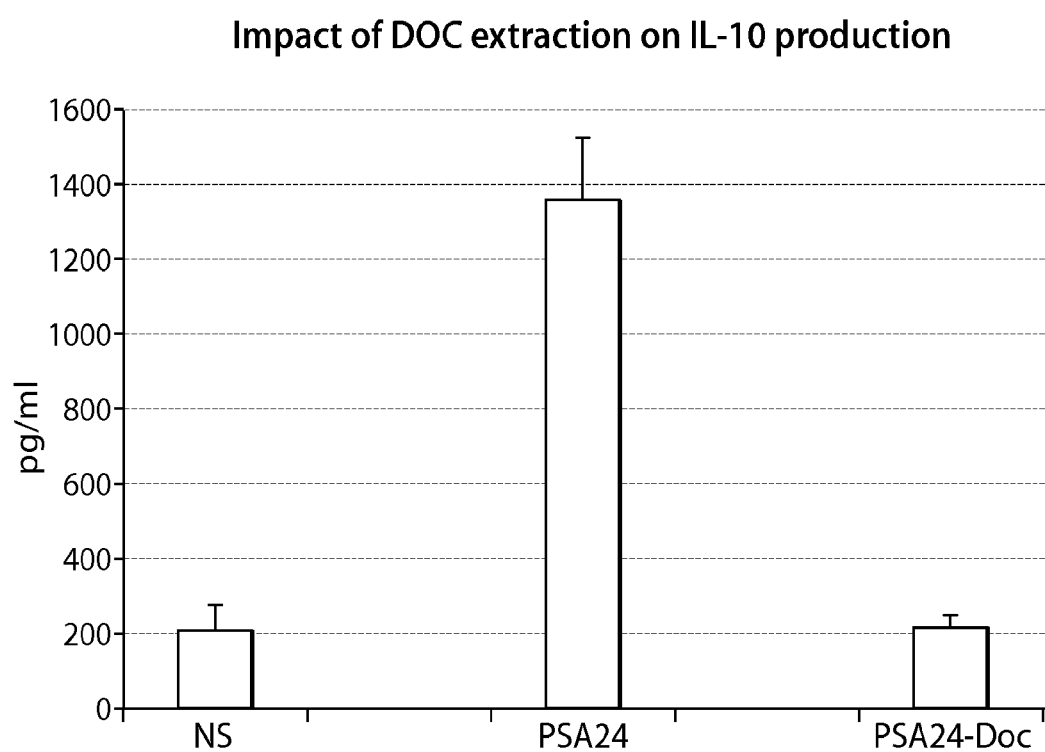
FIG. 9 is a histogram showing the effect of sodium deoxycholate during PSA-LT preparation on IL-10 production.
Figure 10:
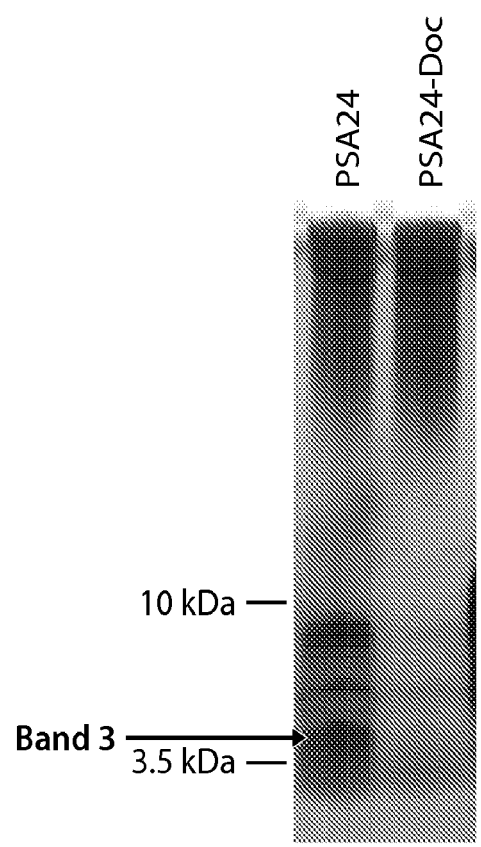
FIG. 10 is a photograph of a gel showing loss of the lipid band (Band 3) after sodium deoxycholate based extraction. The gel in this Figure, as in other Figures, is a 16.5% Tris-Tricine-SDS-PAGE gel that is reversed-stained with zinc sulphate and imidazole.

Another major difference in our purification protocol for PSA-LT, compared to our previous isolation process for PSA, is the elimination of a chromatography step in a sodium deoxycholate (DOC) containing buffer. The difference in activity as a result of contact with DOC is shown in FIG. 9. Lot 24 PSA-LT was suspended in the DOC containing buffer under the pH 9 conditions used in our purification of PSA. The pH of the DOC was 8.0, but the pH was quickly brought up to pH 9 with NaOH and back again with dilute HCl. After extensive dialysis, Lot 24 lost its ability to induce IL-10 in the DC T cell co-culture system. In FIG. 10, Band 3 which is seen after hydrolysis of PSA-LT (Lot 24) is no longer seen after hydrolysis of DOC-treated Lot 24. The elimination of the DOC containing step represents a major departure from all earlier protocols and differentiates methods used currently for preparation of PSA-LT from methods used for preparation of PSA.

C. In Vivo Efficacy of PSA-LT Compared to PSA in an Animal Model of Multiple Sclerosis (EAE).

Figure 11:
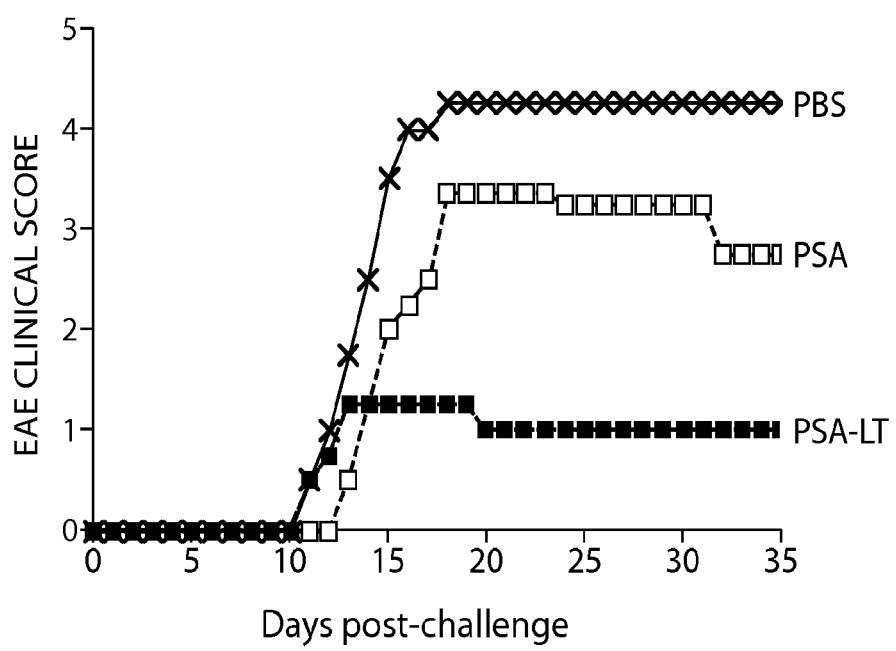
FIG. 11 is a graph showing the effect of non-lipidated (PSA) and lipidated (PSA-LT) forms of PSA on outcome in an experimental autoimmune encephalitis (EAE) animal model system.
Figure 12:
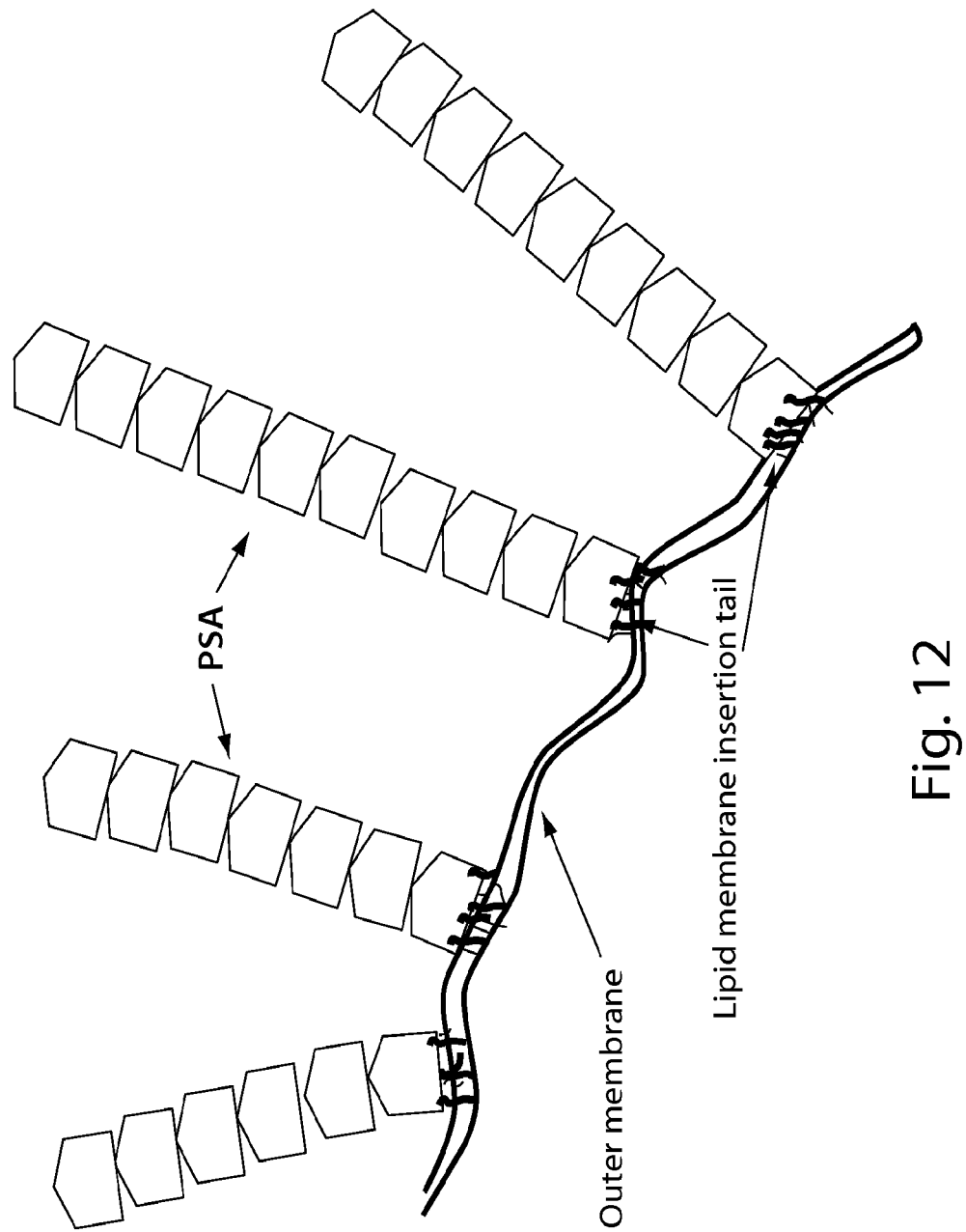
FIG. 12 is a schematic illustrating an embodiment of PSA-LT attachment to the outer membrane of B. fragilis.

The above data demonstrate a significant in vitro enhancement of IL-10 induction in DC T cell co-cultures by PSA-LT when compared to PSA. To determine whether this enhancement of IL-10 production in vitro represented a potential therapeutic advantage in vivo, we compared PSA-LT (Lot 24) with PSA (Lot 23) (FIG. 11). Groups of 6 week old female naïve C57 BL/6 mice were treated with 100 µg of either PSA-LT, PSA, or phosphate buffered saline (PBS) every three days starting 6 days before EAE induction. Mice were challenged subcutaneously with 250 µg of $MOG_{33-55}$ (Peptides International) in 200 µl of complete Freund's adjuvant (Sigma). On days 0 and 2 after challenge, mice received intraperitoneal injections of 250 ng of *Bordetella pertussis* toxin (List Biological Laboratories). Disease was scored on an established 0 to 5 scale, with 5 being advanced neurological disease. Mice were monitored and scored daily for disease progression. When compared to PBS treated controls, animals receiving PSA had a statistically significant reduction in disease severity; however, animals receiving PSA-LT had an even more marked reduction in disease severity with nearly complete protection against the development of EAE.

These studies show a critical enhanced protective capacity of PSA-LT when compared to PSA in a very significant animal model of human disease.

Methods of Detection

The invention provides methods for detecting the presence of PSA-LT and in some instances quantitating the amount of PSA-LT in a sample or a composition. These methods employ the Tris-Tricine SDS-PAGE gel system described herein. Samples are run on such 16.5% Tris-Tricine SDS-PAGE gels and then reverse stained with zinc sulphate and imidazole. The presence of PSA-LT is indicated by the presence of a band at about 5 kD. The major band above 60 kD represents PSA (lipidated or non-lipidated versions).

The compositions analyzed using this system may be obtained as described herein, including for example following a phenol/water extraction, ethanol precipitation, mild acid hydrolysis, and size exclusion, or they may be obtained and/or prepared in other ways.

Methods of Use

The invention provides various methods of in vitro and in vivo use of the compositions provided herein. In vitro uses include use as an analytical tool (e.g., as a marker of the presence of *B. fragilis*) and as an assay standard or control (e.g., as a positive marker of PSA-LT).

In vivo uses include but are not limited to those involving human subjects. For example, in vivo uses include administration of the compositions of the invention to a non-human subject in order to modulate an immune response.

The invention generally provides methods of modulating immune responses in a subject having or likely to develop an aberrant immune response. Typically, the aberrant immune response is an enhanced immune response and the composition acts to down-regulate the immune response. Enhanced immune responses are typically associated with inflammatory conditions, such as but not limited to autoimmune diseases.

Accordingly, the compositions of the invention may be used to modulate (and typically down-regulate) immune responses in subjects having or at risk of developing autoimmune diseases. As will be understood by those of ordinary skill in the art, subjects having autoimmune diseases typically experience one or more "events" or recurrences associated with the autoimmune disease. For example, a subject having inflammatory bowel disease may experience temporally isolated attacks of the disease, characterized by the presence of symptoms or increased severity of symptoms. The invention contemplates that the compositions may be used in such subjects to reduce the likelihood of such future recurrences of the disease or to reduce the severity of symptoms associated with the disease (e.g., pain, fever, discomfort, fatigue, etc.). Thus, the compositions may be administered prior to such recurrence, and in this manner may be chronically administered, optionally at a regular frequency. Examples include once a day, once every 2, 3, 4, 5 or 6 days, or once a week, etc. The invention also contemplates that the compositions may be administered to the subject during a recurrence in order to reduce the severity of symptoms or shorten the time of the recurrence.

Autoimmune diseases are known in the art. Examples of autoimmune diseases include but are not limited to multiple sclerosis, inflammatory bowel disease including Crohn's Disease and ulcerative colitis, rheumatoid arthritis, psoriasis, type I diabetes, uveitis, Celiac disease, pernicious anemia, Srojen's syndrome, Hashimoto's thyroiditis, Graves' disease, systemic lupus erythamatosis, acute disseminated encephalomyelitis, Addison's disease, Ankylosing spondylitis, Antiphospholipid antibody syndrome, Guillain-Barre syndrome, idiopathic thrombocytopenic purpura, Goodpasture's syndrome, Myasthenia gravis, Pemphigus, giant cell arteritis, aplastic anemia, autoimmune hepatitis, Kawaski's disease, mixed connective tissue disease, Ord throiditis, polyarthritis, primary biliary sclerosis, Reiter's syndrome, Takaysu's arteritis, vitiligo, warm autoimmune hemolytic anemia, Wegener's granulomatosis, Chagas' disease, chronic obstructive pulmonary disease, and sarcoidosis.

In important embodiments, the autoimmune disease is multiple sclerosis. In other important embodiments, the autoimmune disease is an inflammatory bowel disease including but not limited to ulcerative colitis and Crohn's disease.

In some instances, the compositions of the invention may be administered to a subject who has yet to manifest an autoimmune disease (including symptoms thereof) yet is at risk of developing such as disease based on a known genetic or familial predisposition. Such a subject may have one or more family members that are afflicted with the disease.

In some instances, the compositions of the invention are administered to subject having or at risk of developing graft-versus-host disease. Administration may occur prior to, during and/or after transplantation of an organ or tissue (including blood or a blood product) into the subject.

In still other instances, the compositions may be administered to subjects having or at risk of developing a conditions associated with inflammation.

As an example, the composition may be administered to a subject having asthma. As will be understood in the art, subjects having asthma typically experience asthmatic attacks or events characterized by impaired breathing. The invention contemplates that the compositions described herein may be administered acutely (e.g., a single large dose) or chronically (e.g., repeated, smaller doses) to asthmatic subjects. Accordingly, in some instances, the compositions may be administered prior to an asthmatic attack in order to prevent the occurrence of the attack, reduce the frequency of attacks, and/or to lessen the severity of the attack. In some instances, the compositions may be administered during an attack in order to reduce its severity and/or reduce its duration.

Another condition associated with inflammation is a post-surgical adhesion. The invention contemplates administration of the compositions described herein to subjects having or at risk of developing a post-surgical adhesion. The compositions may be administered prior to, during, and/or immediately following surgery in order to prevent the occurrence of such adhesions and/or reduce their severity. The compositions may be administered repeatedly following surgery, including for example every day, every two days, every three days, etc. for a week, two weeks, three weeks, a month, or several months post-surgery.

Another condition associated with inflammation is an abscess, including but not limited to an abdominal abscess as may occur upon leakage of intestinal contents into the peritoneum. In these instances, the subjects being treated may also be administered anti-bacterial agents such as antibiotics.

Another condition associated with inflammation is obesity, and accordingly the invention also contemplates administration of the compositions described herein in subjects that are obese. Such subjects are typically defined as having a body mass index (BMI) of 30 or more. In some instances, the compositions may be administered to a subject having a BMI greater than 20 or greater than 25. The compositions are intended to prevent further weight gain and/or induce weight loss in such subjects.

A subject intends any subject that would benefit from administration of a composition of the invention or that could be administered the composition of the invention. In important embodiments, the subject is a human subject. The subject may also be a companion animal such as a dog or cat, agricultural livestock such as horses, cattle, pigs, sheep, etc., laboratory animals such as mice, rats, rabbits, monkeys, etc., or animals such as those maintained in zoos or otherwise in captivity.

A variety of administration routes are available. The particular mode selected will depend, of course, upon the particular condition being treated, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, inhalation, or parenteral routes. The term "parenteral" includes subcutaneous, intravenous, intramuscular, intraperitoneal, or infusion.

Formulations

When administered, the active agents of the invention are formulated as pharmaceutically acceptable compositions or preparations. Such compositions or preparations may routinely contain pharmaceutically acceptable carriers, concentrations of salt, buffering agents, preservatives, other immune modulators, and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being comingled with active agents of the present invention, in a manner such that there is no interaction which would substantially impair the desired pharmaceutical efficacy.

The pharmaceutical compositions may conveniently be presented in unit dosage form and may be prepared by any of the methods well-known in the art of pharmacy. All methods include the step of bringing PSA-LT (and/or compositions comprising PSA-LT) into association with a carrier which constitutes one or more accessory ingredients. In general, the compositions are prepared by uniformly and intimately bringing the PSA-LT composition into association with a liquid carrier, a finely divided solid carrier, or both, and then, if necessary, shaping the product. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

The active agent may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal intravenous, etc. administrations may be found in Remington's Pharmaceutical Sciences, Mack Publishing Company, Easton, Pa.

The pharmaceutical preparations, as described above, are administered in effective amounts. For therapeutic applications, it is generally that amount sufficient to achieve a medically desirable result. In general, a therapeutically effective amount is that amount necessary to delay the onset of, inhibit the progression of, or halt altogether the particular condition being treated, including reducing the likelihood, frequency and/or severity of a recurrence of the condition. As an example, the effective amount may be that amount which serves to reduce, alleviate, or delay the onset of the symptoms (e.g., pain, fever, etc.) of the disorder being treated or prevented. The effective amount will depend upon the mode of administration, the particular condition being treated and the desired outcome. It will also depend upon the stage of the condition, the severity of the condition, the age and physical condition of the subject being treated, the nature of concurrent therapy, if any, the duration of the treatment, the specific route of administration and like factors within the knowledge and expertise of the medical practitioner. For prophylactic applications, it is that amount sufficient to delay the onset of, inhibit the progression of, or halt altogether the particular condition being prevented, and may be measured by the amount required to prevent the onset of symptoms.

Generally, doses of active compounds of the present invention may be from about 0.01 mg/kg per day to 1000 mg/kg per day, preferably from about 0.1 mg/kg to 200 mg/kg and most preferably from about 0.2 mg/kg to about 20 mg/kg, in one or more dose administrations daily, for one or more days. It is expected that doses ranging from 1-500 mg/kg, and preferably doses ranging from 1-100 mg/kg, and even more preferably doses ranging from 1-50 mg/kg, will be suitable. The preferred amount can be determined by one of ordinary skill in the art in accordance with standard practice for determining optimum dosage levels of the agent. It is generally preferred that a maximum dose is the highest safe dose according to sound medical judgment be used.

In some instances, the total daily dose for a human subject may range from about 50-100 micrograms of PSA-LT.

The pharmaceutical preparation may be administered alone or in conjunction with other compounds. In one embodiment the pharmaceutical preparation is given in conjunction with one or more anti-bacterial agents including antibiotics selected from the group consisting of penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin.

The following Examples are included for purposes of illustration and are not intended to limit the scope of the invention.

EXAMPLES

Example 1

Summary of Isolation of PSA-LT (Lot 24, PSA24)

B. fragilis was grown in anaerobic conditions. The capsular complex from B. fragilis was isolated with hot phenol/water extraction. PSA-LT was precipitated with ethanol after DNAse, RNAse and pronase treatments. The precipitate was then acid treated with 2% acetic acid at 90° C. for 3 hours. PSA-LT was further purified on S-400 size exclusion column in PBS. The fractions were analyzed and pooled, then dialyzed and lyophilized. The purity of PSA was assessed by nuclear magnetic resonance spectroscopy and SDS PAGE gel, as described herein.

Example 2

Specific Isolation of PSA-LT (Lot 24, PSA24)

The isolation and purification process of PSA-LT is provided below in greater detail.

B. fragilis strain 9343 which overexpresses polysaccharide A (PSA) was plated onto a blood agar plate and grown overnight at 37° C. A swab from a heavily colonized plate was sub-cultured into a 500 ml starter culture of peptone yeast broth. The starter culture was inoculated into 16 liter culture of the same media and pH was titrated to neutrality with 5M NaOH. An anaerobic gas mix was bubbled into the sealed culture.

After an overnight culture maintained at pH 7, bacteria were checked by Gram stain and subculture. Organisms were collected by centrifugation at 8,000×g for 20 minutes. Bacterial pellets were washed two times with saline yielding approximately one liter of bacterial pellet.

The bacterial pellet was suspended in 68° C. melted crystalline phenol to a final concentration of phenol of about 37% v/v (yielding a phenol/water preparation) and mixed for 30 minutes at 68° C. followed by stirring at 4° C. for 48 hours. The phenol/water preparation was aliquoted into glass bottles which were then centrifuged at 1500 rpm. The upper water layer was harvested. Any residual phenol contained in the harvested aqueous phase was extracted with an equal volume of ethyl ether. The ether phase was then removed using a separatory funnel and any residual ether in the aqueous phase was evaporated, yielding the final aqueous phase from the phenol/water preparation.

The aqueous phase was dialyzed versus water with multiple changes over 5 days at 4° C. and subsequently lyophilized until it was nearly dry (approximately 5 ml water remaining). 0.05M Tris with magnesium, calcium and sodium azide (total volume 61 ml) was added to the lyophilized product to bring the total volume to about 66 ml.

To the dissolved product was added 10 ml of Tris buffer with DNase (0.07 mg/ml) and RNAase (0.33 mg/ml). The entire suspension was filtered through a 0.45 micron filter and the filtrate was stirred at 37° C. The DNase/RNAase treatment was repeated by adding fresh enzyme to the mixture, at similar concentrations, and stirred for two hours.

The pH of the mixture was then raised to 7.5 with 2M NaOH and 25 mg pronase in 10 ml Tris/magnesium/calcium solution was added and the mixture stirred for 24 hours at 37° C. This step was repeated.

The PSA-LT was precipitated by adding 5 volumes of ethanol at 4° C. to the mixture. The solution was then centrifuged at 12,000×g for 30 minutes to pellet PSA-LT. The supernatant was removed and the pellet was resuspended in 392 ml type 1 $H_2O$.

Acid treatment was then carried out by adding 8 mls acetic acid to the solution, and heating it for three hours at 90° C. The solution was then cooled slightly, neutralized with NaOH, and cooled to 4° C.

Following repeat centrifugation, precipitate was discarded and the supernatant was dialyzed against two changes of 16 liters type 1 $H_2O$ at 4° C. The volume was reduced by lyophilization to approximately 50 mls. Twenty ml aliquots were chromatographed on a 5×200 cm column of S400 suspended in PBS and fractions were collected. Fractions were tested by double diffusion in agar with an antibody that reacts with both lipidated and non-lipidated PSA to determine where PSA-LT eluted. PSA-LT was found in fractions 46 to 88, as shown in FIG. 1. Aliquots of these were tested for UV absorption at 280 nm and it was determined that PSA-LT containing fractions had no UV absorbable material.

Fractions containing PSA-LT were then pooled and concentrated and dialyzed against type 1 $H_2O$ on a Minitan concentrator (Millipore) with 10,000 mw cutoff membranes until conductivity of 100 ml was less than 50 µS.

PSA-LT was then lyophilized. Recovery of total PSA was 739 mg.

The degree of contaminating LPS was determined by Pro Q LPS stain on an SDS PAGE gel system and determined to be approximately 0.5%. Polysaccharide purity and structure was determined by proton nuclear magnetic resonance spectroscopy on a 600 mHz spectrometer.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. 'one or the other but not both') when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, 'at least one of A and B' (or, equivalently, "at least one of A or B," or, equivalently 'at least one of A and/or B') can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A pharmaceutical composition comprising:
    an isolated lipidated polysaccharide A (PSA) comprising a PSA polysaccharide covalently conjugated to a lipid, and
    a pharmaceutically-acceptable carrier or excipient, wherein the composition is suitable for administration to a human.

2. The pharmaceutical composition of claim 1, wherein the lipid represents 0.1-2% (w/w) of the lipidated PSA.

3. The pharmaceutical composition of claim 1, wherein the lipid represents less than 1% (w/w) of the lipidated PSA.

4. The pharmaceutical composition of claim 1, wherein the composition is substantially free of LPS.

5. The pharmaceutical composition of claim 1, wherein the pharmaceutically-acceptable carrier or excipient is orally-acceptable, and the composition is a formulation for oral delivery.

6. The pharmaceutical composition of claim 1, wherein the lipid and PSA are covalently conjugated by a bond that is not susceptible to cleavage by snake venom phosphodiesterase.

7. The pharmaceutical composition of claim 1, wherein the lipidated PSA comprises 99% PSA (w/w) and 0.5% lipid (w/w).

8. The pharmaceutical composition of claim 1, wherein the lipidated-PSA is isolated from *B. fragilis* cells that overexpress PSA relative to a parental strain of *B. fragilis*, under conditions that maintain the lipid conjugated to PSA.

9. The pharmaceutical composition of claim 1, wherein the lipidated PSA comprising polysaccharide A (PSA) covalently conjugated to a lipid, is in a lyophilized form.

10. A pharmaceutical composition comprising isolated lipidated polysaccharide A (PSA) comprising polysaccharide A (PSA) covalently conjugated to a lipid.

11. The pharmaceutical composition of claim 1, wherein the pharmaceutical composition is sterile.

12. The pharmaceutical composition of claim 1, further comprising a preservative.

13. The pharmaceutical composition of claim 5, wherein the formulation for oral delivery is selected from the group consisting of a capsule, tablet, lozenge, syrup, elixir or an emulsion.

14. The pharmaceutical composition of claim 5, wherein the lipidated PSA is characterized by being soluble in an aqueous solution.

15. A pharmaceutical composition formulated for oral administration, the composition comprising:
    a preparation of an isolated polysaccharide whose structure comprises a tetrasaccharide repeating unit as set forth below:

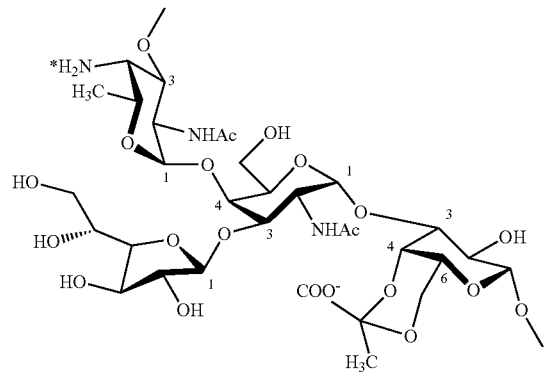

which preparation comprises the isolated polysaccharide conjugated to a non-LPS lipid; and
    a pharmaceutically acceptable carrier;
    wherein the composition is essentially free of a *B.fragilis* nucleic acid and/or protein.

16. The pharmaceutical composition of claim 15, further comprising an immune modulator other than the preparation of polysaccharide.

* * * * *

UNITED STATES PATENT AND TRADEMARK OFFICE
CERTIFICATE OF CORRECTION

PATENT NO.         : 9,539,281 B2                                          Page 1 of 1
APPLICATION NO.    : 14/131812
DATED              : January 10, 2017
INVENTOR(S)        : Dennis L. Kasper et al.

It is certified that error appears in the above-identified patent and that said Letters Patent is hereby corrected as shown below:

On the Title Page

Item (74) should read:
(74) *Attorney, Agent or Firm* – Wolf, Greenfield & Sacks, P.C.

In the Claims

In Claim 15, at Column 18, the structure shown should be replaced with the following:

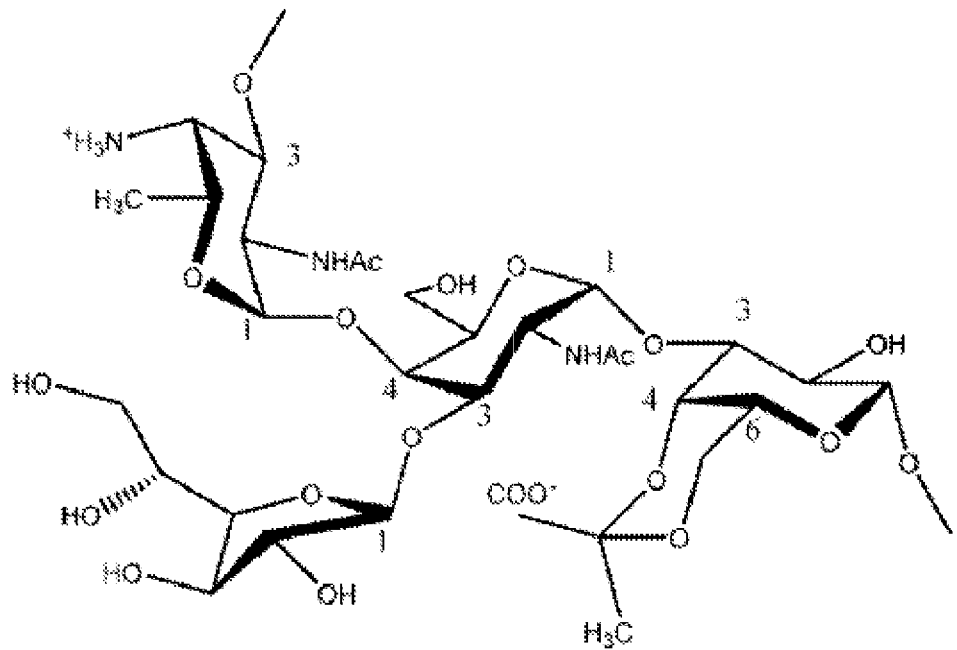

Signed and Sealed this
Thirtieth Day of May, 2017

Michelle K. Lee
*Director of the United States Patent and Trademark Office*